(12) United States Patent
Offutt et al.

(10) Patent No.: US 12,274,878 B2
(45) Date of Patent: Apr. 15, 2025

(54) LOW HEALTHCARE PROVIDER INTERACTION AND OUTCOME BASED PROGRAMMING

(71) Applicant: Medtronic, Inc., Minneapolis, MN (US)

(72) Inventors: Sarah J. Offutt, Golden Valley, MN (US); Nicholas Reid Singer, Minneapolis, MN (US); Katie C. Bittner, White Bear Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 593 days.

(21) Appl. No.: 17/453,611

(22) Filed: Nov. 4, 2021

(65) Prior Publication Data

US 2022/0143403 A1 May 12, 2022

Related U.S. Application Data

(60) Provisional application No. 63/198,716, filed on Nov. 6, 2020.

(51) Int. Cl.
*A61N 1/36* (2006.01)
*A61N 1/05* (2006.01)
*A61N 1/372* (2006.01)

(52) U.S. Cl.
CPC ....... *A61N 1/36007* (2013.01); *A61N 1/0551* (2013.01); *A61N 1/36132* (2013.01); *A61N 1/36146* (2013.01); *A61N 1/37235* (2013.01)

(58) Field of Classification Search
CPC .............. A61N 1/36007; A61N 1/0551; A61N 1/36132; A61N 1/36146; A61N 1/37235
See application file for complete search history.

(56) References Cited

U.S. PATENT DOCUMENTS 6,463,328 B1  10/2002  John
7,305,268 B2  12/2007  Gliner et al.
(Continued)

FOREIGN PATENT DOCUMENTS

EP    3473294 A1    4/2019
WO    2000/01320 A2  1/2000
(Continued)

OTHER PUBLICATIONS

Amend et al., How Does Sacral Modulation Work Best? Placement and Programming Techniques to Maximize Efficacy,: Current Urology Reports, vol. 12, No. 5, Jun. 2011, 9 pp.
(Continued)

*Primary Examiner* — Mark W. Bockelman
(74) *Attorney, Agent, or Firm* — Shumaker & Sieffert, P.A.

(57) ABSTRACT

A medical system for treating incontinence includes an implantable medical device (IMD) implantable proximate to a tibial nerve of a patient comprising therapy delivery circuitry configured to provide electrical stimulation therapy proximate the tibial nerve of the patient for treating incontinence, and processing circuitry configured to: during an implant period, determine a set of stimulation parameters to control the therapy delivery circuitry, during an induction period after the implant period, initiate electrical stimulation therapy according to the set of stimulation parameters, during a first maintenance period, determine an adjustment to the set of stimulation parameters as first maintenance period stimulation parameters to reduce the electrical stimulation therapy from the induction period, and during a second maintenance period, determine an adjustment to the set of stimulation parameters as second maintenance period stimulation parameters to reduce the electrical stimulation therapy from the first maintenance period.

20 Claims, 8 Drawing Sheets

(56) References Cited

U.S. PATENT DOCUMENTS

| | | | |
|---|---|---|---|
| 7,369,894 B2 | 5/2008 | Gerber | |
| 7,801,618 B2 | 9/2010 | Pless | |
| 7,853,323 B2 | 12/2010 | Goetz | |
| 8,204,597 B2 | 6/2012 | Gerber et al. | |
| 8,554,331 B2 | 10/2013 | Gerber et al. | |
| 8,615,299 B2 | 12/2013 | Goetz | |
| 8,702,629 B2 | 4/2014 | Giuffrida et al. | |
| 8,731,656 B2 | 5/2014 | Bourget et al. | |
| 8,792,991 B2 | 7/2014 | Gerber et al. | |
| 8,805,508 B2 | 8/2014 | Gerber et al. | |
| 8,874,217 B2 | 10/2014 | Alataris et al. | |
| 8,989,861 B2 | 3/2015 | Su et al. | |
| 9,272,140 B2 | 3/2016 | Gerber | |
| 9,555,246 B2 | 1/2017 | Jiang et al. | |
| 9,561,372 B2 | 2/2017 | Jiang et al. | |
| 9,592,004 B2 | 3/2017 | DiLorenzo et al. | |
| 9,649,439 B2 | 5/2017 | John | |
| 9,669,219 B2 | 6/2017 | Caparso et al. | |
| 9,956,404 B2 | 5/2018 | Brink et al. | |
| 9,959,388 B2 | 5/2018 | Grandhe et al. | |
| 10,004,901 B2 | 6/2018 | Gliner | |
| 10,029,102 B2 | 7/2018 | Doan et al. | |
| 10,076,667 B2 | 9/2018 | Kaula et al. | |
| 10,118,037 B2 | 11/2018 | Kaula et al. | |
| 10,124,171 B2 | 11/2018 | Kaula et al. | |
| 10,265,532 B2 | 4/2019 | Carcieri et al. | |
| 10,272,247 B2 | 4/2019 | Bokil et al. | |
| 10,299,987 B2 | 5/2019 | Greiner et al. | |
| 10,315,031 B2 | 6/2019 | Brink et al. | |
| 10,426,949 B2 | 10/2019 | Johnson et al. | |
| 10,561,848 B2 | 2/2020 | Xiao et al. | |
| 10,569,088 B2 | 2/2020 | Dinsmoor et al. | |
| 10,576,283 B2 | 3/2020 | Flaherty et al. | |
| 10,576,293 B2 | 3/2020 | Peterson et al. | |
| 10,625,082 B2 | 4/2020 | Laghi | |
| 10,716,505 B2 | 7/2020 | Blum et al. | |
| 10,729,903 B2 | 8/2020 | Jiang et al. | |
| 11,045,649 B2 | 6/2021 | Wei et al. | |
| 2003/0158583 A1 | 8/2003 | Burnett et al. | |
| 2004/0193228 A1 | 9/2004 | Gerber | |
| 2007/0100388 A1 | 5/2007 | Gerber | |
| 2007/0162086 A1 | 7/2007 | DiLorenzo | |
| 2008/0300449 A1 | 12/2008 | Gerber et al. | |
| 2011/0071589 A1 | 3/2011 | Starkebaum et al. | |
| 2012/0136413 A1* | 5/2012 | Bonde | A61N 1/36007 607/48 |
| 2012/0197338 A1 | 8/2012 | Su et al. | |
| 2013/0079840 A1 | 3/2013 | Su et al. | |
| 2013/0079841 A1 | 3/2013 | Su et al. | |
| 2014/0046397 A1 | 2/2014 | Rohrer et al. | |
| 2014/0046423 A1* | 2/2014 | Rajguru | A61N 2/02 607/144 |
| 2014/0364920 A1 | 12/2014 | Doan et al. | |
| 2016/0004547 A1 | 1/2016 | Mitsuyu | |
| 2016/0045724 A1 | 2/2016 | Lee et al. | |
| 2016/0136420 A1 | 5/2016 | Brink et al. | |
| 2017/0065821 A1 | 3/2017 | Brink et al. | |
| 2017/0239470 A1 | 8/2017 | Wei et al. | |
| 2018/0133484 A1 | 5/2018 | Dinsmoor et al. | |
| 2018/0154144 A1 | 6/2018 | Brink et al. | |
| 2018/0289965 A1 | 10/2018 | Nelson et al. | |
| 2019/0001135 A1 | 1/2019 | Yoo et al. | |
| 2019/0001139 A1 | 1/2019 | Mishra et al. | |
| 2019/0060647 A1 | 2/2019 | Su et al. | |
| 2019/0217092 A1 | 7/2019 | Baynham et al. | |
| 2019/0255331 A1 | 8/2019 | Subbaroyan | |
| 2019/0262609 A1 | 8/2019 | Brill et al. | |
| 2019/0269924 A1 | 9/2019 | Su et al. | |
| 2019/0328303 A1 | 10/2019 | Nelson et al. | |
| 2020/0046974 A1 | 2/2020 | Ostroff et al. | |
| 2020/0147397 A1 | 5/2020 | Huertas Fernandez et al. | |
| 2020/0230406 A1 | 7/2020 | Brink et al. | |
| 2020/0282213 A1 | 9/2020 | Tesfayesus et al. | |
| 2021/0031032 A1 | 2/2021 | Zirpel et al. | |
| 2021/0031033 A1 | 2/2021 | Davies et al. | |
| 2021/0299442 A1 | 9/2021 | Wei et al. | |
| 2021/0316145 A1 | 10/2021 | Offutt et al. | |

FOREIGN PATENT DOCUMENTS

| | | | |
|---|---|---|---|
| WO | 2000/19939 | A1 | 4/2000 |
| WO | 2003/026738 | A1 | 4/2003 |
| WO | 2006/012423 | A1 | 2/2006 |
| WO | 2007/098202 | A2 | 8/2007 |
| WO | 2011/156288 | A2 | 12/2011 |
| WO | 2016/028608 | A1 | 2/2016 |
| WO | 2017/142948 | A1 | 8/2017 |

OTHER PUBLICATIONS

Cadish et al., "Stimulation Latency and Comparison of Cycling Regimens in Women Using Sacral Neuromodulation," Neurourology and Urodynamics, vol. 36, No. 2, Feb. 2017, 4 pp.

Oerlemans et al., "Is on-Demand Sacral Neuromodulation in Patients With OAB Syndrome a Feasible Therapy Regime?", Neurourology and Urodynamics, vol. 30, No. 8, Nov. 2011, 4 pp.

Pineau et al., "Treating epilepsy via adaptive neurostimulation: a reinforcement learning approach." International Journal of Neural Systems, vol. 19, No. 4, Aug. 2009, 14 pp.

Price et al., "Prospective Randomized Crossover Trial Comparing Continuous and Cyclic Stimulation in InterStem Therapy," Female Pelvic Medicine & Reconstructive Surgery, vol. 21, No. 6, Nov./Dec. 2015, 4 pp.

Sandler et al., "Designing Patient-Specific Optimal Neurostimulation Patterns for Seizure Suppression," Neural Computation, vol. 30, No. 5, May 2018, 29 pp.

* cited by examiner

LOW HEALTHCARE PROVIDER INTERACTION AND OUTCOME BASED PROGRAMMING

This application claims the benefit of U.S. Provisional Patent Application No. 63/198,716, filed on Nov. 6, 2020, the entire content of which is incorporated herein by reference.

FIELD

The disclosure is generally related to medical devices and, more particularly, medical devices that deliver therapy to a patient.

BACKGROUND

Disease, age, and injury may impair physiological functions of a patient. In some situations, the physiological functions are completely impaired. In other examples, the physiological functions may operate sufficiently at some times or under some conditions and operate inadequately at other times or under other conditions. Some examples of impaired physiological functions include overactive bladder, non-obstructive urinary retention, fecal incontinence, constipation, neurogenic bladder or bowel function, pelvic pain, and sexual dysfunction. In one example, bladder dysfunction, such as overactive bladder, frequency, urgency, or urinary incontinence, is a problem that may afflict people of all ages, genders, and races. Various muscles, nerves, organs and conduits within the pelvic floor cooperate to collect, store and release urine. A variety of disorders may compromise urinary tract performance, and contribute to an overactive bladder, urgency, frequency, or urinary incontinence that interferes with normal physiological function. Many of the disorders may be associated with aging, injury or illness.

Electrical nerve stimulation may be used for several therapeutic and diagnostic purposes, including the treatment of the aforementioned impaired physiological functions.

SUMMARY

Tibial neuromodulation (TNM) is one example therapy for the treatment of the aforementioned disorders, and tends to be less invasive than stimulating other nerves, such as the sacral nerve(s). This disclosure describes examples of an implantable medical device (IMD) configured to provide stimulation to the tibial nerve (e.g., provide TNM). TNM therapy by an IMD can also be referred to as implantable tibial neuromodulation (ITNM) or implantable tibial neurostimulation (ITNS).

The various example techniques described herein may personalize and optimize the care for each patient based on their disease burden, as well as reduce the practice burden to clinics. Personalized and optimized care may be used to treat OAB (overactive bladder), urinary retention, fecal incontinence, as well as neurogenic function, pelvic pain, and sexual function. For example, the example techniques described herein offer a clinical workflow that steps a patient through therapy with various checkpoints to either increase or decrease therapy regimen based on patient outcomes or patient goals while permitting reduction in unnecessary interaction with clinicians.

As an example, a workflow begins with an induction period, during which it is likely that the IMD delivers a relatively higher stimulation regimen (e.g., the energy of the stimulation signal is higher than what may be needed to treat the symptoms). The therapy induction period can be started the first day of the procedure, eliminating the need for a follow up visit to program the patient's device. During the induction period, the patient receives checkpoints that either allow the patient to enter a maintenance stage with relatively lower stimulation regimens (including timing, amplitude, pattern, etc. of lower energy stimulation), keep the patient at their current stimulation energy setting, or increase the stimulation energy setting of the stimulation regimen. These checkpoints can be done at a physician visit or managed remotely either by a patient programmer or similar platform (e.g. with a healthcare provider (HCP)), so that optimal stimulation is being delivered with minimal office visits. The example techniques may be performed in a cloud based platform as well. As more patients titrate their therapy, stimulation regimens can be analyzed, and recommendations for more effective regimens can be made based on demographics, medical history, symptoms, among others. If the HCP agrees, the HCP does not have to be involved with changes to the stimulation regimen within pre-defined ranges of parameters, ensuring patients get titrated doses specific to their needs while clinicians do not have to spend time managing adjustments in programing. In a maintenance stage, titration of therapy can be decreasing stimulation occurrence or decreasing stimulation amplitude, or both in certain embodiments.

In one example, the disclosure describes a medical system for treating incontinence comprising: an implantable medical device (IMD) implantable proximate to a tibial nerve of a patient, the IMD comprising therapy delivery circuitry configured to provide electrical stimulation therapy proximate the tibial nerve of the patient for treating incontinence; and processing circuitry configured to: during an implant period, determine a set of stimulation parameters to control the therapy delivery circuitry, during an induction period after the implant period, initiate electrical stimulation therapy according to the set of stimulation parameters, during a first maintenance period, determine an adjustment to the set of stimulation parameters as first maintenance period stimulation parameters to reduce the electrical stimulation therapy from the induction period, wherein the therapy delivery circuitry provides the electrical stimulation therapy according to the first maintenance period stimulation parameters, and during a second maintenance period, determine an adjustment to the set of stimulation parameters as second maintenance period stimulation parameters to reduce the electrical stimulation therapy from the first maintenance period, wherein the therapy delivery circuitry provides the electrical stimulation therapy according to the second maintenance period stimulation parameters.

In one example, the disclosure describes a method for treating incontinence, the method comprising: during an implant period, determining, with processing circuitry, a set of stimulation parameters for electrical stimulation therapy to control a therapy delivery circuitry; during an induction period after the implant period, causing, with the processing circuitry, the therapy delivery circuitry to deliver electrical stimulation therapy according to the set of stimulation parameters to a tibial nerve of a patient for treating the incontinence; during a first maintenance period, determining, with the processing circuitry, an adjustment to the set of stimulation parameters as first maintenance period stimulation parameters to reduce the electrical stimulation therapy from the induction period; causing, with the processing circuitry, the therapy delivery circuitry to deliver the electrical stimulation therapy according to the first maintenance period stimulation parameters to the tibial nerve of the patient for treating the incontinence; during a second maintenance period, determining, with the processing circuitry, an adjustment to the set of stimulation parameters as second maintenance period stimulation parameters to reduce the electrical stimulation therapy from the first maintenance period; and causing, with the processing circuitry, the therapy delivery circuitry to deliver the electrical stimulation therapy according to the second maintenance period stimulation parameters to the tibial nerve of the patient for treating the incontinence.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1A:
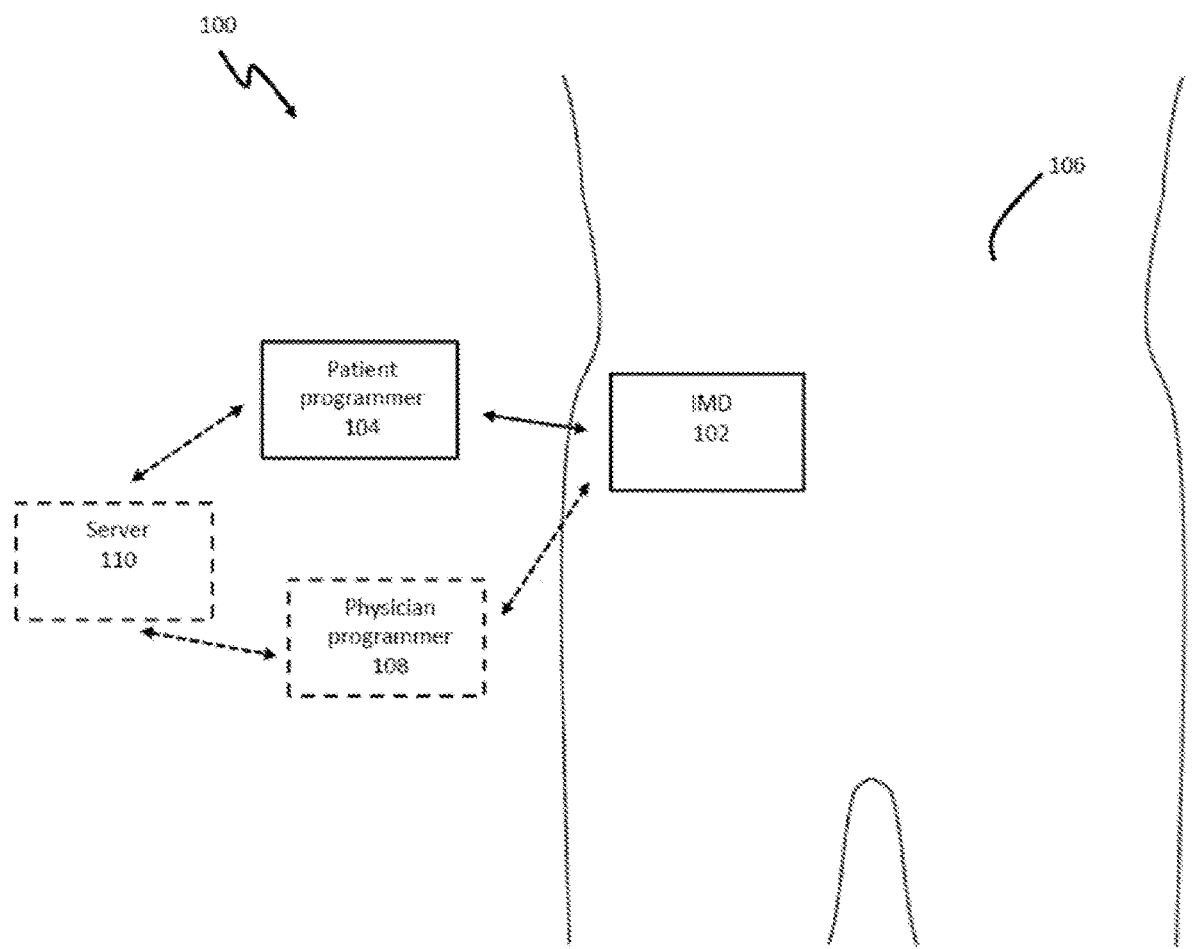
FIG. 1A is a conceptual diagram illustrating an example system that manages delivery of neurostimulation to a patient, according to one or more examples.

The example techniques described in this disclosure relate to stimulation for treating incontinence (e.g., urinary and/or fecal incontinence). To treat incontinence, an implantable medical device (IMD) may be configured to output electrical stimulation therapy to stimulate one or more nerves such as tibial nerve(s), sacral nerve(s), a pudendal nerve, etc. In some examples, a patient response to the electrical stimulation therapy can change over time. For instance, after implant of the IMD, the IMD may deliver an electrical stimulation therapy having a first set of stimulation parameters to provide effective treatment. Then, over time, it may be possible to reduce the amount of electrical stimulation therapy that is needed to achieve effective treatment.

For instance, in one or more examples, there may be an "induction period," during which the IMD may deliver the electrical stimulation therapy having the first set of stimulation parameters. With the delivery of the electrical stimulation therapy having the first set of stimulation parameters, the central nervous system may become "induced." The central nervous system being induced may refer to the central nervous system being conditioned to respond to the therapy. As an example, after initial implantation, the amount of stimulation needed to achieve therapeutic benefit may be relatively high or the patient may not experience therapeutic benefit even with a relatively high amount of stimulation. However, during this time of delivery of a relatively high energy amount of stimulation (i.e., during the induction period), the central nervous system may become induced.

In one or more examples, after the induction period, the IMD may be configured to deliver therapy in accordance with a maintenance period. In the maintenance period, the IMD may deliver the electrical stimulation therapy having a second set of stimulation parameters. The electrical stimulation therapy having the second set of stimulation parameters may include one or more reduced parameter values yielding reduced energy electrical stimulation therapy relative to the electrical stimulation therapy having the first set of stimulation parameters.

From neurophysiological perspective, the induction period is when the patient is undergoing some changes, for example reorganization/alterations in synaptic response which leads to the initial effect. It may be the case that introduction of stimulation "normalizes" the patient back to the organization similar to in healthy individuals. In order to establish this response, for example, a certain frequency (number of presentations of the stimulation) is needed. The patient may not reorganize or establish a new state if the stimulation is not presented enough.

Once the patient reaches that effect, the nervous system may not need the stimulation presented at the same frequency. Rather, the nervous system may need periodic stimulation to remain in a therapeutic state.

In other words, in the induction period, the patient needs to be stimulated a sufficient amount of time and/or at a sufficient amplitude so that the patient is conditioned for the therapy. For example, prior to the induction period, the amount of stimulation (e.g., in terms of stimulation session duration, stimulation session occurrence, and/or amplitude) that the patient needs for therapeutic effect (e.g., to stay in a therapeutic state) may be at a first amount of stimulation. During the induction period, the delivery of the stimulation conditions the patient (e.g., changes the state of the patient) such that at the end of induction period, the amount of stimulation that the patient needs for therapeutic effect (e.g., to stay in a therapeutic state) may be at a second amount of stimulation that is less than the first amount of stimulation. For example, in the maintenance period, less amount of stimulation may be needed to cause the nervous system to operate similar to have a therapeutic response, such as achieve continence. In some examples, the induction period may also change the sensitivity of these nerves or the sensitivity of the nerves upstream (e.g., spinal cord) such that less stimulation is needed in the maintenance period to keep the patient in a therapeutic state.

Transitioning from induction period to maintenance period should not be confused with titrating of therapy or a patient simply increasing or decreasing therapy. Transitioning from the induction period to the maintenance period may be when the patient has been conditioned in a way in which less stimulation is sufficient to achieve effective treatment. For titration or manual increase and decrease of therapy, often times patients increase the stimulation level to have sensation. However, in the techniques described in this disclosure, the stimulation is reduced during the maintenance periods when the patient has been conditioned in accordance with the induction period.

There may be various ways in which to reduce the electrical stimulation therapy, such as based on reduction of a stimulation session duration and/or frequency of stimulation session occurrence. Stimulation session duration may refer to the amount of time for which stimulation is delivered. The electrical stimulation therapy may include a plurality of pulses having an amplitude, pulse width, and frequency, and the stimulation session duration may define for how long the plurality of pulses are delivered. The amplitude, pulse width, and frequency may be examples of the stimulation parameters, and the stimulation session duration may be another example of the stimulation parameters.

Stimulation session occurrence may refer to how often stimulation is delivered. For instance, the stimulation session occurrence may define how often the plurality of pulses are delivered. Similar to above, the stimulation session occurrence may be another example of the stimulation parameters. Stimulation session occurrence and stimulation frequency should not be confused. Stimulation session occurrence may refer to how often the patient receives the plurality of pulses, and the stimulation frequency may define characteristics of the plurality of pulses (i.e., how often or the rate at which a stimulation pulse is delivered).

As one example way to reduce the electrical stimulation therapy from the induction period to the maintenance period, during the induction period, the IMD may deliver the induction period therapy (i.e., the electrical stimulation therapy having the first set of stimulation parameters) for a first stimulation session duration (e.g., 24 hours of stimulation therapy, 12 hours of stimulation therapy, etc.). During the maintenance period, the IMD may deliver the maintenance period therapy (i.e., the electrical stimulation therapy having the second set of stimulation parameters) for a second stimulation session duration (e.g., 30 minutes of stimulation therapy) that is less than the first duration. In this example, the first set of stimulation parameters and the second set of stimulation parameters may define different stimulation session durations.

As another example way to reduce the electrical stimulation therapy from the induction period to the maintenance period, during the induction period, the IMD may deliver the induction period therapy (i.e., the electrical stimulation therapy having the first set of stimulation parameters) for a first stimulation session occurrence (e.g., once a day, once every two days, etc.). During the maintenance period, the IMD may deliver the maintenance period therapy (i.e., the electrical stimulation therapy having the second set of stimulation parameters) for a second stimulation session occurrence (e.g., once a week, once every two weeks, etc.) that is less frequent than the first stimulation session occurrence. In this example, the first set of stimulation parameters and the second set of stimulation parameters may define different stimulation session occurrences.

There may be other ways to reduce the electrical stimulation therapy from the induction period to the maintenance period. For example, it may be possible to reduce the electrical stimulation therapy by reducing the amplitude, pulse width, or frequency of stimulation pulses. In some examples, without limitation, amplitude may be a preferred way to reduce the energy of the electrical stimulation therapy, as the pulse width and frequency may define how many nerve fibers are been activated.

In accordance with techniques described in this disclosure, the IMD may be configured to transition from the induction period to the maintenance period with minimal need for clinical intervention, and deliver electrical stimulation therapy that is personalized for the patient. For example, in some examples, after implant, the IMD may deliver electrical stimulation therapy during the induction period. During various checkpoints before the maintenance period, the patient may indicate whether changes to the stimulation parameters are appropriate (e.g., based on patient outcomes or patient goals). Based on the response to the checkpoint, the IMD may remain operating in accordance with the induction period based on patient feedback, possibly with updated stimulation parameters. In some examples, IMD may transition to operating in accordance with the maintenance period based on patient feedback.

As described above, in the maintenance period, the amount of stimulation therapy being delivered by the IMD is reduced (e.g., one or combination of reduction of stimulation session duration parameter, reduction in stimulation session occurrences parameter, reduction in amplitude parameter, etc.). In some examples, within the maintenance period there may be a plurality of checkpoints. During a maintenance period checkpoint, based on patient feedback, it may be possible to further reduce the amount of stimulation therapy being delivered or revert back to an earlier, higher amount of stimulation therapy being delivered.

Referring to FIG. 1A, a conceptual diagram illustrating an example system 100 that manages delivery of neurostimulation to a patient is depicted, according to one or more examples. System 100 generally comprises an IMD 102 and a patient programmer 104 operably coupled to IMD 102.

IMD 102 can be implanted in patient 106. IMD 102 is configured to provide electrical stimulation therapy to a target tissue site corresponding to a nerve of patient 106 by generating a programmable electrical stimulation signal (e.g., in the form of electrical pulses) and delivering the electrical stimulation signal to a target tissue site. In one or more examples, IMD 102 includes a lead of one or more stimulation electrodes implanted on the nerve such that the target tissue site is the nerve itself. In one or more examples, IMD 102 is positioned adjacent to the nerve such that the electrical stimulation is delivered from IMD 102 to a target tissue site adjacent to the nerve via the stimulation electrodes.

The example techniques described in this disclosure may be used with a variety of implantable medical devices, including but not limited to nerve stimulation devices (also known as neuro stimulators or neuromodulation devices). In some examples, neuromodulation devices may be used to stimulate a variety of nerves or associated tissues for treating a variety of conditions. Electrical stimulation may be delivered for spinal cord stimulation (SCS), peripheral nerve stimulation (PNS), peripheral nerve field stimulation (PNFS), deep brain stimulation (DBS), cortical stimulation (CS), pelvic floor stimulation, sacral nerve stimulation, tibial nerve stimulation, gastric stimulation, and the like.

In an example, the techniques described in this disclosure may be used as part of a system for treating pelvic health conditions including incontinence, overactive bladder, pelvic pain or other pelvic floor disorders. In some instances, the example techniques may be implemented as part of sacral nerve(s) stimulation system.

Figure 1B:
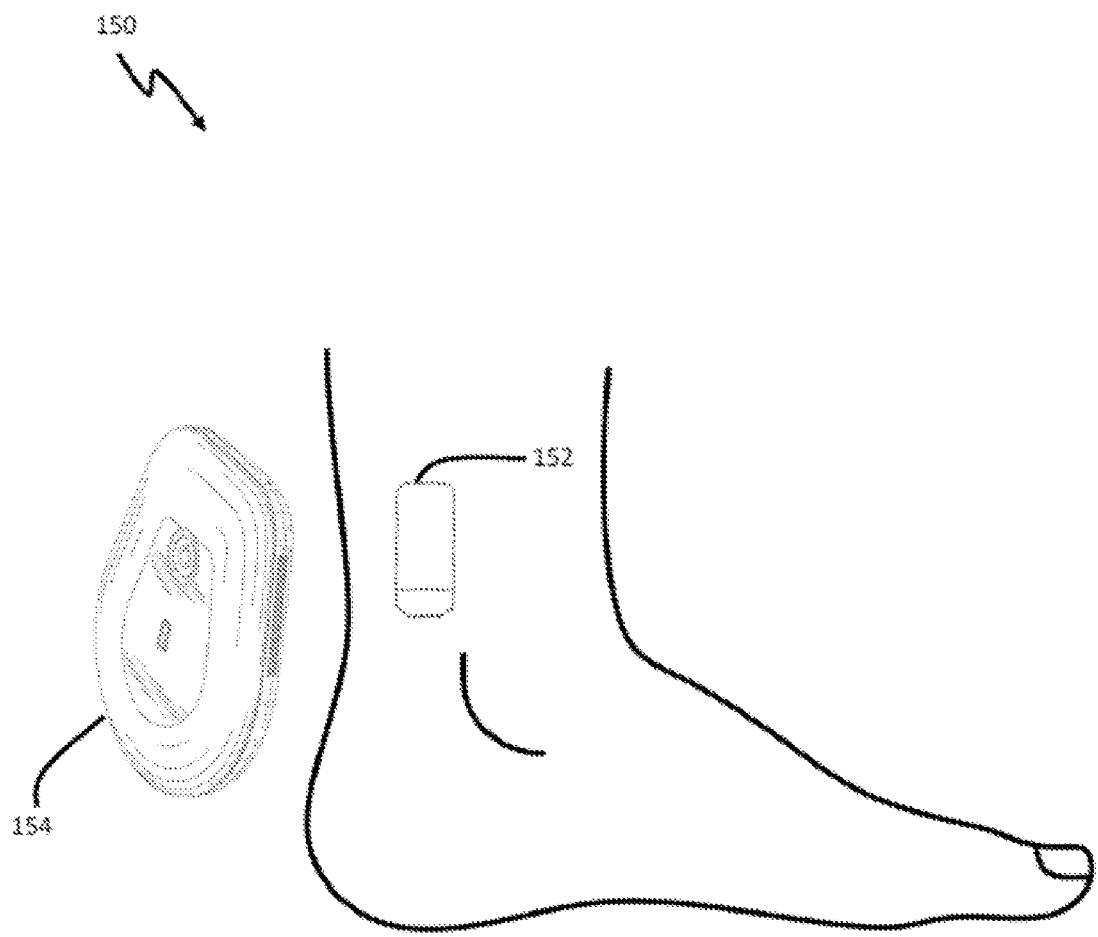
FIG. 1B is a conceptual diagram illustrating an example system that manages delivery of neurostimulation to a patient, according to one or more examples.

Referring to FIG. 1B, in another example pertaining to treatment of pelvic health disorders, the example techniques may be implemented as part of tibial nerve(s) stimulation system 150, including an implantable tibial nerve stimulation device 152 and an external recharger 154, wherein external recharger 154 can be positioned on or proximate to skin of the patient over the location of implantable nerve stimulation device 152 to facilitate recharging. Tibial nerve stimulation system 150 may also include a wearable ankle cuff to hold external recharger 154 in position on an ankle of a patient. In some examples, tibial nerve stimulation system 150 may include a primary cell power source (e.g., non-rechargeable), and external recharger 154 may not be needed in such examples. Tibial nerve stimulation system 150 may stimulate one tibial nerve, both tibial nerves, or alternate stimulation to the tibial nerves. The example techniques are applicable to stimulation of one tibial nerve, both tibial nerves, or alternating stimulation.

Figure 2:
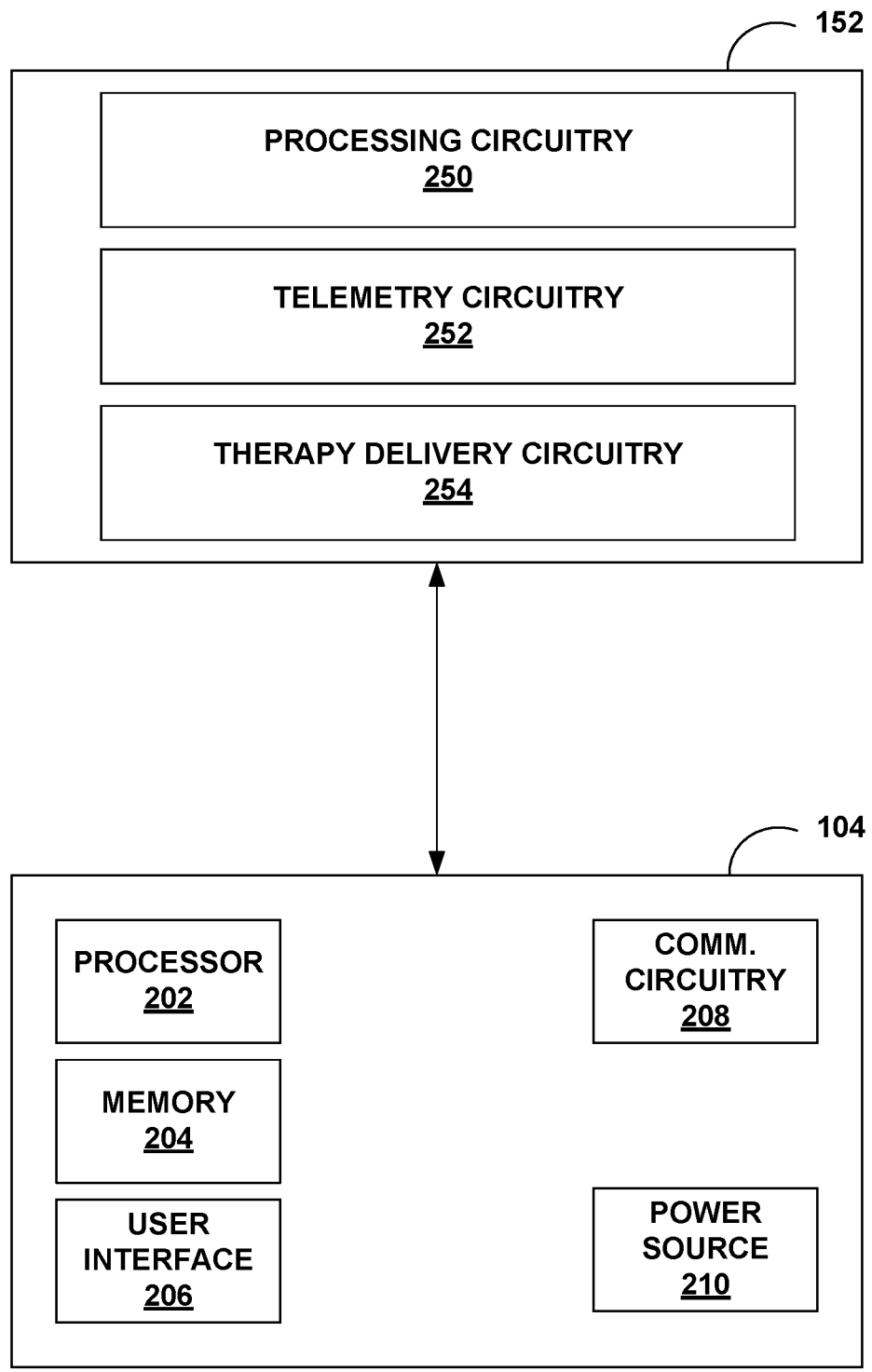
FIG. 2 is a block diagram of an example patient programmer, according to one or more examples.

Accordingly, and referring to FIG. 2, IMD 152 can include processing circuitry 250, telemetry circuitry 252, and therapy delivery circuitry 254. IMD 102 may include similar components as IMD 152. In one or more examples, as will be understood by one of ordinary skill in the art, processing circuitry 250 comprises hardware and/or software to implement the functions of IMD 152. In one or more examples, telemetry circuitry 252 comprises hardware and/or software to communicate with, for example, patient programmer 104. In one or more examples, therapy delivery circuitry 254 is configured to provide electrical stimulation therapy proximate a nerve of a patient (e.g., sacral nerve(s) or tibial nerve).

The electrical stimulation therapy can be used to treat an impaired physiological function such as a bladder dysfunction or bowel dysfunction of patient 106. In one or more examples, the electrical stimulation therapy is implemented by an electrical current, or optionally, an electrical voltage. The electrical stimulation therapy may be defined by a plurality of parameters such as amplitude (e.g., current or voltage amplitude), pulse width, and/or frequency. Example ranges for the amplitude, pulse width, and/or frequency are provided below.

Patient programmer 104 is communicatively coupled to IMD 152 via wireless communication. Referring to FIG. 2, a block diagram of patient programmer 104 is depicted, according to one or more examples. Patient programmer 104 can be a device for inputting information relating to patient 106, receiving information from IMD 152, and updating IMD 152. In some examples, patient programmer 104 can be a wearable communication device, with a therapy request input integrated into a key fob or a wristwatch, handheld computing device, smart phone, computer workstation, or networked computing device. Practically, patient programmer 104 can be a bring-your-own device provided by the patient, or provided by the healthcare provider in connection with the implantable.

Patient programmer 104 generally comprises a processor 202, a memory 204, a user interface 206, communication circuitry 208, and a power source 210. Processor 202 can be any programmable device that accepts digital data as input, is configured to process the input according to instructions or algorithms, and provides results as outputs. In an example, processor 202 can be a central processing unit (CPU) configured to carry out the instructions of a computer program. Processor 202 is therefore configured to perform at least basic arithmetic, logical, and input/output operations. In one or more examples, processor 202 correspond to individual hardware units, such as microprocessors, ASICs, DSPs, FPGAs, or other hardware units. In other examples, processor 202 can correspond to multiple individual hardware units, such as microprocessors, ASICs, DSPs, FPGAs, or other hardware units.

Memory 204 can comprise volatile or non-volatile memory as required by the coupled processor 202 to not only provide space to execute the instructions or algorithms, but to provide the space to store the instructions themselves. In one or more examples, volatile memory can include random access memory (RAM), dynamic random access memory (DRAM), or static random access memory (SRAM), for example. In one or more examples, non-volatile memory can include read-only memory, flash memory, ferroelectric RAM, hard disk, floppy disk, magnetic tape, or optical disc storage, for example. The foregoing lists in no way limit the type of memory that can be used.

User interface 206 can include a button or keypad, lights, a speaker for voice commands, a turnable knob, a display, such as a liquid crystal (LCD), light-emitting diode (LED), or cathode ray tube (CRT). In some examples, the display may be a touch screen. Processor 202 can present and receive information relating to electrical stimulation and resulting therapeutic effects via user interface 206. For example, processor 202 can receive patient input via user interface 206. The input can be, for example, in the form of pressing a button on a keypad or selecting an icon from a touch screen. Processor 202 can also present information to the patient in the form of alerts related to delivery of the electrical stimulation to patient 106 or a caregiver via user interface 206.

Communications circuitry 208 is configured to interface with IMD 152 and optionally, server 110 (FIG. 1), as will be described. Communications circuitry 208 supports wireless communication between IMD 152 and, optionally, between server 110 and patient programmer 104 under the control of processor 202. Communications circuitry 208 can also be configured to communicate with another computing device via wireless communication techniques, or direct communication through a wired connection. Communications circuitry 208 can provide wireless communication via an RF or proximal inductive medium. In some examples, communications circuitry 208 can include an antenna, which may take on a variety of forms, such as an internal or external antenna.

Examples of local wireless communication techniques that may be employed to facilitate communication between patient programmer 104 and another computing device include RF communication according to the 802.11 or Bluetooth specification sets, infrared communication, e.g., according to the IrDA standard, or other standard or proprietary telemetry protocols. In this manner, other external devices may be capable of communicating with patient programmer 104 without needing to establish a secure wireless connection.

Power source 210 delivers operating power to the components of patient programmer 104. Power source 210 can include a battery and a power generation circuit to produce the operating power. In some examples, the battery may be rechargeable by for example, an exterior power source.

Accordingly, as will be described, patient programmer 104 allows the patient to adjust therapy parameters (e.g., amplitude, frequency, and/or pulse width) and to activate or execute other maintenance periods. Further, patient programmer 104 can communicate with IMD 152 to update the functionality of IMD 152.

Referring again to FIG. 1A, system 100 may further optionally comprises a physician programmer 108. Physician programmer 108 can be substantially similar to patient programmer 104, but be configured for physician operation or control. Accordingly, physician programmer 108 can likewise update the functionality of IMD 152, and program therapy parameters similar to patient programmer 104. In some examples, patient programmer 104 may be constrained in the amount and types of changes patient programmer 104 can make (e.g., maximum and minimum changes to value of therapy parameters). Physician programmer 108 may provide additional flexibility to the physician or clinician in setting parameters that may not be available with patient programmer 104.

As illustrated in FIG. 1A, system 100 further optionally comprises a server 110. Server 110 can include one or more servers in a cloud computing environment. Server 110 can be configured to communicate with patient programmer 104, physician programmer 108 and/or IMD 102 (not shown for ease of illustration) via wireless communication through a network access point. Server 110 can be co-located with patient programmer 104 or physician programmer 108, or located elsewhere, such as in a cloud computing data center.

Server 110 can be programmed by a physician user, including by physician programmer 108 or by another interface to server 110. Server 110 can store stimulation regimens, therapy parameters, and/or patient population statistics in response to such stimulation regimens and therapy parameters to guide future therapies of IMD 102. In some examples, a user can also interact with patient programmer 104, physician programmer 108, server 110 and/or IMD 102 remotely via a networked computing device. Although the above example in FIG. 1A is described with respect to IMD 102, the above examples may be applicable to IMD 152 to FIG. 1B.

In some examples, the various processing operations and components described herein can be implemented on IMD 102 or IMD 152. In some examples, the various processing operations and components described herein can be implemented on patient programmer 104. In some examples, the various processing operations and components described herein can be implemented on server 110. In some examples, the various processing operations and components described herein can be implemented on physician programmer 108. In some examples, the various processing operations and components described herein can be split between multiple components, such as patient programmer 104, physician programmer 108, 110, and/or IMD 102 or IMD 152.

In accordance with one or more examples described in this disclosure, IMD 102 and/or IMD 152 may be configured to deliver electrical stimulation therapy to the patient to address incontinence (e.g., urinary or fecal incontinence). Examples of the incontinence include urge urinary incontinence (UUI), urinary frequency (UF), fecal incontinence (FI), and other pelvic floor indications that can be treated with tibial neuromodulation. For ease, the examples are described with respect to IMD 152, but the example techniques are applicable to IMD 102 as well.

In one or more examples, IMD 152 may be configured to deliver different amounts of electrical stimulation therapy based on a therapy period. For instance, during an implant period (e.g., as part of implanting IMD 152 or shortly after implanting IMD 152 while the patient is in clinic), IMD 152 may determine a set of stimulation parameters to control therapy delivery circuitry 254. As one example, the set of stimulation parameters may be according to a sensory threshold (e.g., a level at which the patient experiences paresthesia or otherwise "feels" the therapy) and/or a motor threshold (e.g., a level at which there is muscle movement due to the therapy or an electromyography (EMG) signal). For example, during or after implant, the HCP may increase the amplitude, pulse width, and/or frequency from a baseline level until the patient indicates that he or she feels the therapy. The HCP may use physician programmer 108 to output the therapy parameters that resulted in the patient feeling the therapy to IMD 152. To determine the set of stimulation parameters, IMD 152 may receive the set of stimulation parameters from physician programmer 108.

In some examples, the stimulation parameters may be based on sensed signals, such as sensed evoked compound action potential (eCAP) or electromyography (EMG) signals. For instance, therapy delivery circuitry 254 may output a signal that evokes a compound action potential (e.g., eCAP signal). Sensing circuitry of IMD 152 may sense the eCAP, and compare the eCAP to a threshold. Based on the comparison, IMD 152 may determine stimulation parameters.

After implant, it may be possible for IMD 152 to start delivering therapy in accordance with the set of stimulation parameters (e.g., those determined according to a sensory and/or motor threshold). However, it may not be necessary to keep therapy at the initial set of stimulation parameters. Rather, over time, it may be possible to reduce the amount of electrical stimulation therapy that is delivered, as the patient may experience therapeutic benefits even with lower electrical stimulation therapy. The amount of electrical stimulation therapy may refer to the energy of pulses (e.g., amplitude, frequency, pulse width), stimulation session occurrence, and stimulation session duration.

For instance, after implant, during an induction period, IMD 152 may be configured to deliver electrical stimulation therapy at a relatively higher stimulation regimen. For instance, IMD 152 may be configured to deliver electrical stimulation therapy for a relatively extended period of time (e.g., for an extended stimulation session duration), may be configured to deliver electrical stimulation therapy relatively often (e.g., for a relatively higher rate of stimulation session occurrence), and/or may be configured to deliver electrical stimulation therapy at a relatively higher energy level, e.g., with a relatively higher amplitude. In some examples, the induction period may be started on the first day of the implant procedure, eliminating the need for a follow up visit to program IMD 152.

In accordance with one or more examples, during the induction period, the patient may provide checkpoint information of whether to enter a maintenance period, stay in the induction period with current parameter settings, or stay in the induction period but with updated parameter settings. The patient may provide such checkpoint information as part of a workflow based on desired patient outcomes or patient goals. The checkpoints may be done at a visit to the HCP or managed without or outside of a visit to the HCP with patient programmer 104 so that optimal stimulation may be delivered with minimal visits to the HCP.

Based on patient outcomes or patient goals, after the induction period, IMD 152 may be configured to operate in accordance with a maintenance period. In the maintenance period, the amount of electrical stimulation delivered to the patient may be reduced, without impact on effectiveness of therapy. For example, there may be a reduction in a stimulation session duration (e.g., a stimulation session duration in the maintenance period is less than a stimulation session duration of the induction period stimulation parameters). As an example, if the stimulation session duration during the induction period is four hours of stimulation, then in the maintenance period the stimulation session duration may be 30 minutes.

As another example, there may be a reduction in a stimulation session occurrence (e.g., a stimulation session occurrence in the maintenance period is less than a stimulation session occurrence of the induction period stimulation parameters). As an example, if the stimulation session occurrence during the induction period is every day, then in the maintenance period the stimulation session occurrence may be once a week or once every two weeks.

In some examples, the stimulation parameters in the maintenance period may include a reduction in both the stimulation session duration and the stimulation session occurrence. For example, if the stimulation session duration was four hours in the induction period, and the stimulation session occurrence was once a day, then in the maintenance period, the stimulation session duration may be 30 minutes (or less), and the stimulation session occurrence may be once every week or once every two weeks.

The above examples of 30 minutes of stimulation every week or every other week is provided as an example only. In some examples, the range of stimulation session duration may be 1 minute to 1 hour (e.g., range of 1 minute to 10 minutes, 10 minutes to 15 minutes, 15 minutes to 30 minutes, or 30 minutes to one hour), and the range of the stimulation session occurrence may be once a day to once a month (e.g., once a day, once every two days, once every three days, once every four days, once every five days, once every six days, once a week, once every two weeks, once a month, and any time in between). The stimulation session duration and/or stimulation session occurrence may be different for induction and maintenance periods. However, other ranges are possible, and the techniques are not limited to the above example ranges. Moreover, there may be additional other ways to reduce stimulation such as by reducing amplitude of the stimulation.

In some examples, the stimulation session duration for the maintenance periods may be a certain percentage of the stimulation session duration for the induction periods (e.g., stimulation session duration for the maintenance periods is less than 10%, less than 20%, less than 30%, less than 40%, or less than 50% of the stimulation session duration for the induction periods). In some examples, the stimulation session occurrence for the maintenance periods may be a certain percentage of the stimulation session occurrence for the induction periods (e.g., stimulation session occurrence for the maintenance periods is less than 10%, less than 20%, less than 30%, less than 40%, or less than 50% of the stimulation session occurrence for the induction periods).

Also, in the above examples, there is one maintenance period. However, the example techniques are not so limited. For instance, in some examples, there may be a plurality of maintenance periods, and during respective checkpoints, the patient may indicate whether he or she is experiencing the desired patient outcomes. If the patient is experiencing the desired patient outcomes, during a first maintenance period, IMD 152 may be configured to deliver stimulation in accordance with a second maintenance period. For instance, there may be a set of stimulation parameters that therapy delivery circuitry 254 outputs, where the amount of electrical stimulation therapy that is delivered is less than the amount of electrical stimulation therapy that is delivered during the first maintenance period (e.g., in terms of stimulation session duration, stimulation session occurrence, stimulation amplitude, etc.).

For example, during an implant period (e.g., as part of the implant or during the visit when IMD 152 is implanted), processing circuitry 250 may determine a set of stimulation parameters to control therapy delivery circuitry 254 (e.g., according to a sensory threshold and/or motor threshold). During an induction period, processing circuitry 250 may initiate electrical stimulation therapy according to the set of stimulation parameters.

In some examples, during a first maintenance period, processing circuitry 250 may determine an adjustment to the set of stimulation parameters as first maintenance period stimulation parameters to reduce the electrical stimulation therapy from the induction period. During the first maintenance period, therapy delivery circuitry 254 may provide (e.g., output) the electrical stimulation therapy according to the first maintenance period stimulation parameters.

During a second maintenance period, processing circuitry 250 may determine an adjustment to the set of stimulation parameters as second maintenance period stimulation parameters to reduce the electrical stimulation therapy from the first maintenance period. During the second maintenance period, therapy delivery circuitry 254 may provide (e.g., output) the electrical stimulation therapy according to the second maintenance period stimulation parameters.

There may be a plurality of maintenance periods. For example, during a third maintenance period, processing circuitry 250 may determine an adjustment to the set of stimulation parameters as third maintenance period stimulation parameters to reduce the electrical stimulation therapy from the second maintenance period. In some examples, the patient may desire to return from stimulation parameters of the current maintenance period to stimulation parameters of an earlier maintenance period. In such examples, processing circuitry 250 may receive a command to return to stimulation parameters of an earlier maintenance period (e.g., receive a command to return to the first maintenance period from the second maintenance period).

There may be various ways in which processing circuitry 250 may determine a set of stimulation parameters to control therapy delivery circuitry 254 (e.g., according to a sensory or motor threshold), determine an adjustment to the set of stimulation parameters as first maintenance period stimulation parameters to reduce the electrical stimulation therapy from the induction period, and/or determine an adjustment to the set of stimulation parameters as second maintenance period stimulation parameters to reduce the electrical stimulation therapy from the first maintenance period. As one example, IMD 152 (e.g., in memory of IMD 152) may store the sets of stimulation parameters for the induction period, and the different maintenance periods. As another example, IMD 152 may receive from clinician programmer 108 or patient programmer 104 the sets of stimulation parameters for the induction period, and the different maintenance periods. For instance, the patient may program, select, or adjust from a menu the sets of stimulation parameters.

Moreover, in the above example, there may be one induction period. For instance, if the patient is unsatisfied with the therapy, rather than transitioning to the maintenance period, the patient may remain in the induction period. This may be because the patient has not been induced. As an example, it may take more than 3 weeks for the patient to be induced, such that transition to the maintenance period is possible. In some examples, it may be possible to check with the patient after 3 weeks to determine if the therapy is working as desired. If the patient indicates that the therapy is not working, then it is possible that the patient has not yet been induced, and keeping the stimulation parameters as-is is desirable to give the patient additional time to be induced, and then check again after some time.

However, in some cases, the reason why the patient is not experiencing effective therapy may not be because the patient is not induced and needs more time, but rather because the therapy is truly insufficient to cause the patient to be induced. For instance, if the amplitude of the therapy is too low, then regardless of how long therapy is delivered in the induction period, the patient may not experience induction. As another example, if the pulse width is too low, then not enough fibers of the tibial nerve are being activated, and the patient may not experience induction regardless of how long therapy is delivered.

In one or more examples, if the patient indicates during an induction period checkpoint that there is no change or that the patient is unhappy with the outcome, processing circuitry 250 (or possible processing circuitry of programmers 104 and/or 108, and possibly in combination with processing circuitry 250) may determine whether new induction parameters are appropriate. For example, if a threshold amount of time has passed or the patient has been checked on a threshold number of times, the processing circuitry (e.g., any one or combination of processing circuitry 250 or processing circuitry of programmers 104 and 108) may determine that an update to the parameters is desired. The processing circuitry may update the parameters (e.g., increase amplitude, pulse width, frequency, duration, occurrence, etc.). IMD 152 may remain configured in the induction period with the updated parameters, and this process may repeat until the patient is happy with the outcome of therapy.

In some examples, the updated parameters from the induction period may be used to determine the stimulation parameters for the maintenance period (e.g., the first maintenance period). For instance, it may be desirable to not change the pulse width and frequency determined during the induction period because these parameters may define the number of fibers that are activated. Therefore, for the maintenance period(s), the pulse width and frequency determined during the induction period may be maintained, but the amplitude, duration, and/or session occurrence may be reduced.

Accordingly, in one or more examples, after the first induction period and prior to the first maintenance period, processing circuitry 250 may determine to update the set of stimulation parameters (e.g., because the threshold amount of time has elapsed, or threshold number of check-ins with the patient has been reached). Based on the determination to update the set of stimulation parameters, processing circuitry 250 may update the set of stimulation parameters (e.g., by receiving the updated stimulation parameters from programmers 104 or 108 or from memory).

During a second induction period, processing circuitry 250 may initiate electrical stimulation therapy according to the updated set of stimulation parameters. In such examples, during the first maintenance period, to determine the adjustment to the set of stimulation parameters as the first maintenance period stimulation parameters to reduce the electrical stimulation therapy from the induction period, processing circuitry 254 may be configured to, during the first maintenance period, determine an adjustment to the updated set of stimulation parameters as the first maintenance period stimulation parameters to reduce the electrical stimulation therapy from the second induction period.

However, in some examples, there may not be an update to parameters as part of the induction period. For example, after the induction period and prior to the first maintenance period, processing circuitry 250 may determine not to update the set of stimulation parameters (e.g., because the threshold amount of time has not elapsed, or threshold number of check-ins with the patient has not been reached). Based on the determination not to update the set of stimulation parameters, processing circuitry 250 may maintain the electrical stimulation therapy from the induction period.

Figure 3:
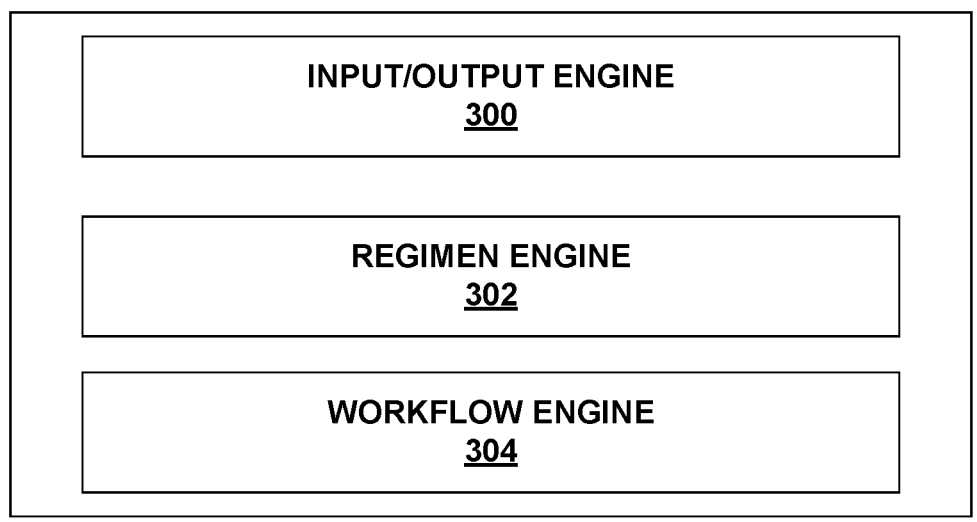
FIG. 3 is a block diagram of various engines implemented by a patient programmer, according to one or more examples.

Referring to FIG. 3, a block diagram of the various engines implemented by a programmer (e.g., patient programmer 104 or physician programmer 108) is depicted. The engines depicted can utilize the components of patient programmer 104, such as processor 202, memory 204, user interface 206, communication circuitry 208, and power source 210 to implement functionality in coordination with IMD 102 or IMD 152.

Some of the subsystems of patient programmer 104 include various engines or tools, each of which is constructed, programmed, configured, or otherwise adapted, to autonomously carry out a function or set of functions. The term engine as used herein is defined as a real-world device, component, or arrangement of components implemented using hardware, such as by an application specific integrated circuit (ASIC) or field-programmable gate array (FPGA), for example, or as a combination of hardware and software, such as by a microprocessor system and a set of program instructions that adapt the engine to implement the particular functionality, which (while being executed) transform the microprocessor system into a special-purpose device.

An engine can also be implemented as a combination of the two, with certain functions facilitated by hardware alone, and other functions facilitated by a combination of hardware and software. In certain implementations, at least a portion, and in some cases, all, of an engine can be executed on the processor(s) of one or more computing platforms that are made up of hardware (e.g., one or more processors, data storage devices such as memory or drive storage, input/output facilities such as network interface devices, video devices, keyboard, mouse or touchscreen devices, etc.) that execute an operating system, system programs, and application programs, while also implementing the engine using multitasking, multithreading, distributed (e.g., cluster, peer-peer, cloud, etc.) processing where appropriate, or other such techniques.

Accordingly, each engine can be realized in a variety of physically realizable configurations, and should generally not be limited to any particular implementation exemplified herein, unless such limitations are expressly called out. In addition, an engine can itself be composed of more than one sub-engines, each of which can be regarded as an engine in its own right. Moreover, in the examples described herein, each of the various engines corresponds to a defined autonomous functionality; however, it should be understood that in other contemplated examples, each functionality can be distributed to more than one engine. Likewise, in other contemplated examples, multiple defined functionalities may be implemented by a single engine that performs those multiple functions, possibly alongside other functions, or distributed differently among a set of engines than specifically illustrated in the examples herein.

As illustrated in FIG. 3, the engines implemented by patient programmer can include an input/output engine 300, a regimen engine 302, and a workflow engine 304. The engines described herein can be implemented by processor 202 using memory 204, along with other subcomponents as described herein.

Input/output engine 300 may be configured to receive inputs from the IMD and/or user and transmit outputs to the user or to the IMD. For example, input/output engine 300 can utilize user interface 206 and/or communications circuitry 208. For example, the patient may interact with input/output engine 300 to provide the sets of stimulation parameters for the different periods (e.g., implant period, induction period, and/or maintenance period).

Regimen engine 302 is configured with various regimen protocols and parameters. In one or more examples, regimen engine 302 can comprise a database or other memory of regimen protocols and parameters. For example, regimen engine 302 may store information for the different sets of parameters used for implant, induction, and maintenance periods. As one example, the different sets of parameters may be stored in a menu form that input/output engine 300 displays, and with which the patient interacts to select the desired set of stimulation parameters.

Workflow engine 304 is configured to utilize the inputs from input/output engine 300, based on data from regimen engine 302 to execute the various workflows described herein. For example, in the above examples, workflow engine 304 may output questions requesting the patient to respond for the different checkpoints. That is, the patient may provide information for the checkpoints as to whether the patient is experiencing therapeutic benefit through workflow engine 304. Workflow engine 304 may utilize the information provided by the patient to determine whether to transition from induction period to the maintenance period, whether additional induction periods are appropriate, and/or whether to transition from one maintenance period to another maintenance period.

Figure 4:
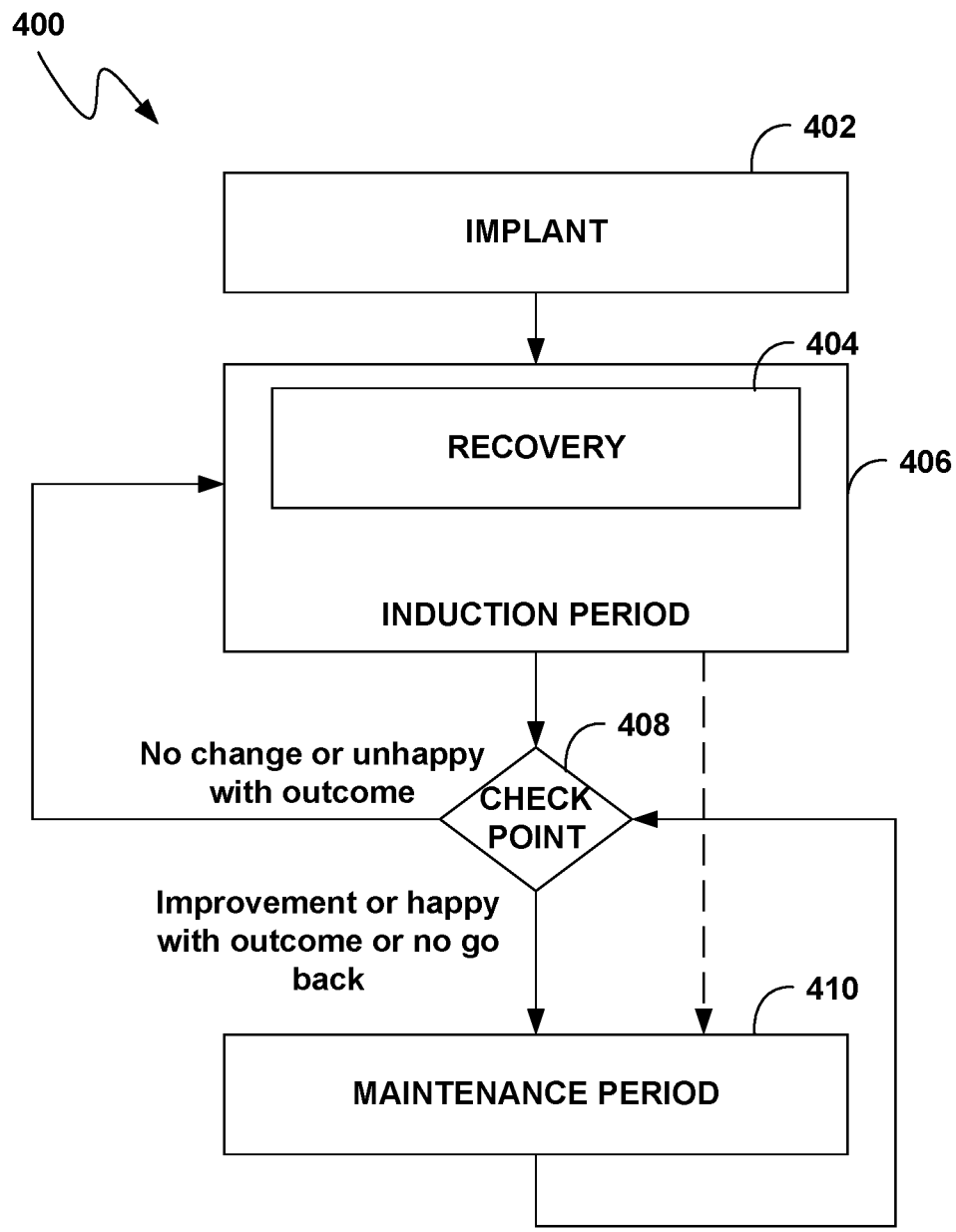
FIG. 4 is a flowchart of a method of optimizing treatment for a medical device, according to one or more examples.

Referring to FIG. 4, a flowchart of a method 400 of optimizing treatment for a medical device is depicted, according to one or more examples. Method 400 can be implemented by, for example, system 100 (or system 150, though reference to system 100 is made for ease of explanation). More particularly, the workflow control can be executed in patient programmer 104. In some examples, the workflow control can be executed by server 110. In some examples, the workflow control can be executed by physician programmer 108 and/or patient programmer 104. In some examples, the workflow control can be executed across multiple components of system 100, such as patient programmer 104, physician programmer 108, and/or server 110.

At 402, an IMD is implanted in a patient. For example, IMD 102 can be implanted in patient 106. IMD can be a constant current (or optionally, constant voltage) electrical stimulation device configured to deliver electrical stimulation pulses for therapy. In some examples, a constant current device is not as beholden to impedances changes as would be a constant voltage. Constant current or constant voltage refers to the current or voltage source being controlled or regulated, and therefore, constant regardless of impedance. However, the amount of constant current or constant voltage can be adjusted.

An IMD having a constant current may ensure that the same current is being delivered to the tissue as impedance changes, and may thereby at least partially account for impedance changes. Amplitude adjustments by the patient or the workflow described herein can still be utilized due to minor changes in the IMD 102 interaction with the patient; for example, the nerve accommodating the stimulation, IMD 102 moving slightly toward or away from the nerve, and so on.

In a constant voltage example, in addition to changing stimulation parameters based on the workflow described herein, there can also be an increase in voltage as impedance increases. If IMD 102 is not capable of increasing voltage, operational algorithms can accommodate for increases in amplitude based on general impedance increase trends.

Further at 402, a motor threshold and one or more sensory thresholds can be tested to set initial stimulation parameters. For example, during the implant or post implant in-clinic programming, a series of simple tests to determine motor and sensory thresholds may be collected. Typically, motor threshold information is collected during the implant procedure and sensory threshold information is collected post-op in-clinic as the patient can report when they feel stimulation. Some examples can also include the location of the motor and sensory information (e.g., where on the patient's body the sensation was felt or visualized).

Such testing allows the patient to turn on IMD 102 immediately after implant or after surgical pain is gone. In some examples, the physician can also configure the implant (i.e., IMD 102) to start in X days and Y time of day from implant, or at a given day and time.

From 402, method 400 enters a recovery period 404. In some examples, a typical recovery period 404 lasts 0-4 weeks. Recovery period 404 can include a sub-process to increase stimulation to account for adaptation. For example, as described herein, different subroutines can be implemented for constant current compared to constant voltage examples. In some examples, the IMD 102 can find or adjust a threshold using patient input.

Recovery time during the recovery period 404 does not require a return trip to the healthcare provider. Unlike some TNM therapies, the correct amplitude setting can be defined intraoperatively, and the patient can turn on (and adjust) their therapy at the time of their choosing. For example, if the amplitude is too high and uncomfortable, the patient can turn down amplitude. Follow ups (ex: incision inspection or programming) can be done remotely, significantly reducing practice burden.

Method 400 further includes an induction period 406. An induction period 406 can overlap with recovery period 404, as illustrated. In some examples, a typical induction period 406 lasts 0-12 weeks. In some examples, induction period 406 utilizes initial stimulation parameters (regimen).

Stimulation parameters can include pulse width, stimulation frequency, amplitude, stimulation session occurrence, and stimulation session duration. For example, induction period 406 can utilize typical TNM stimulation parameters: 20 Hz frequency, 200 microseconds pulse width, tolerable or sensory amplitude (e.g., an amplitude at which the stimulation is still tolerable or is felt by the patient), but be delivered more often or for longer durations per session (e.g., 1 hour every other day or 30 minutes every other day compared to 30 minutes weekly) as compared to maintenance period. Further, higher or lower pulse frequency can be given for different indications. As an example, a regimen can be: stimulation frequency between 1-1000 Hz (in an embodiment stimulation frequency is set to 20 Hz); amplitude: tolerable, sensory or fraction of sensory (e.g., an amplitude at which the stimulation can be felt by the patient or a fraction of such an amplitude); pulse width: between 20-600 microseconds. In some examples, higher stimulation frequency may tend to cause suppression of the nerve activity and the pulse width may define which nerve fibers are activated.

In some examples, the initial stimulation parameters comprise stimulation parameters providing the highest possible stimulation (e.g., highest stimulation energy). Stimulation energy may refer to the energy in the stimulation signal, and may be based on the amplitude, pulse width, frequency, duration, etc. For instance, the stimulation energy of a stimulation signal may be increased or decreased by increasing or decreasing the amplitude, pulse width, frequency, duration, etc. For ease of description, changes in the stimulation (e.g., changes in the simulation energy) are described with respect to increasing or decreasing amplitude, but stimulation energy may be controlled by any one or any combination of amplitude, frequency, pulse width, duration, etc.

Highest possible stimulation may refer to the stimulation level at which the patient experiences therapeutic benefits without negative impact. There may be some discomfort at the highest possible stimulation. For example, at a given frequency and pulse width, during the induction period 406, the HCP or the patient may increase the amplitude of the stimulation signal to the maximum level without having negative impact.

In another example, the initial stimulation parameters comprise stimulation parameters providing a particular therapeutic amplitude such as maximum tolerable to the patient. For example, at a given frequency and pulse width, during the induction period 406, the HCP or the patient may increase the amplitude of the stimulation signal until the patient experiences discomfort, and set the amplitude at a level at which the patient feels little to no discomfort.

In another example, the initial stimulation parameters comprise stimulation parameters at a sensory threshold (e.g., the amplitude is set at a level where paresthesia or some other sensation that stimulation is being delivered is perceived by the patient). At the sensory threshold, the paresthesia or other sensation may not be uncomfortable, but may be noticeable. In another example, the initial stimulation parameters are set based on the patient's disease burden, patient's indication, and/or symptoms.

For example, initial stimulation parameters can include cycles that start as high as 8 hours per day (including continuous) or as low as 30 minutes once per week. In general, induction period 406 comprises a single type of stimulation, with an amplitude defined during or immediately post-implant. The goal of induction period 406 is a higher dosing (longer per day, more times per week) can get the patient to a new state.

In some examples, patient population data from other patients having similar treatments can be utilized to set the induction period 406 regimen. In some examples, parameters can be based on a particular indication. For example, a fecal incontinence treatment may require longer stimulation time per session compared to a urinary incontinence treatment. The number of leaks/voids per day can indicate that a higher session occurrence should be utilized compared to other patients having the same indication but fewer leaks/voids per day.

Referring again to the contrast between OAB and FI, stimulation for the treatment of OAB can target a duration of the latter part of the filling phase when the bladder is more full. A typical treatment using PTNM is 30 min per day, since the duration of the fill/void cycle is about 2-3 hours. In some examples, IMD 102 may be likely to be applying stimulation when the bladder is somewhat full. For bowel, the cycles are much longer (1-2 empties per day max); accordingly, if stimulation is applied for a longer duration (e.g. multiple hours per day), TNM can be more effective because the stimulation is applied when the bowel is in its more full state.

In some examples, for retention, parameters can be based on a number of catheterizations and a pain score (e.g., pelvic pain score). For patients having multiple indications, a priority can be given to those that are most bothersome.

From induction period 406, method 400 proceeds to checkpoint 408. At check point 408, the patient can be prompted or have otherwise provided (e.g., a diary) data corresponding to patient outcomes or goals.

In some examples, checkpoint 408 can include a prompt in the form of a question from patient programmer 104—"Are you doing better? Are you happy with your outcome? Rate your symptoms?", and then a suggestion to move to a particular maintenance period. In some examples, checkpoint 408 can include a tele-visit with an HCP. In some examples, a patient can input diary entries throughout the therapy such that the check point is an evaluation of existing data rather than a specific prompt.

From checkpoint 408, and based on the data provided or otherwise captured, the stimulation regimen can be increased, remain the same, or decreased. For example, from checkpoint 408, if there is no symptom relief or if it is determined at check point 408 that the patient is unhappy with the outcome of therapy, method 400 returns to induction period 406.

Alternatively, from checkpoint 408, if there is improvement in symptom relief or if it is determined at check point 408 that the patient is happy with the outcome of therapy, method 400 proceeds to maintenance period 410. While maintenance period 410 is depicted as a single block, as will be further described with respect to FIG. 5, there may be examples of transitioning between various maintenance periods.

From maintenance period 410, method 400 can return to checkpoint 408. In some examples, a new stimulation regimen is configured at maintenance period 410, and checkpoint 408 is then utilized to step patient stimulation up or down. The new stimulation regimen can be selected from a preselected group, selected by the patient, or programmed.

In the above examples, checkpoint 408 is described in some examples as being an opportunity for the patient to indicate whether the patient is happy or unhappy with the outcome, such as by interacting with programmer 104. However, the example techniques are not so limited.

In FIG. 4, the dashed line from induction period 406 to maintenance period 410 indicates that in some examples checkpoint 408 may be skipped. For instance, for some patients, utilizing programmer 104 may be difficult. Some patients may be well equipped to utilize programmer 104, but may fail or forget to provide responses at checkpoint 408 (e.g., the patient is prompted at checkpoint 408 but fails to take any action).

In some examples, the clinician may program IMD 102 to automatically transition from induction period 406 to maintenance period 410 after a certain amount of time or after a certain number of times that the patient failed to respond during checkpoint 408. There may be various ways in which the clinician may determine how long to wait or how many failed checkpoint instances there are before automatically transitioning IMD 102 from the induction period to the maintenance period. For instance, the clinician may determine when to automatically transition IMD 102 from the induction period to the maintenance period based on population statistics or determined during initial programming.

In some examples, rather than automatically transitioning from induction period 406 to maintenance period 410, the patient may request the clinician to transition from induction period 406 to maintenance period 410. In some examples, the clinician may remotely control IMD 102 to transition from induction period 406 to maintenance period 410. In some examples, the clinician may transition IMD 102 from induction period 406 to maintenance period 410 during a clinician visit.

As illustrated, after maintenance period 410, there is another checkpoint 408. In examples where checkpoint 408 is skipped, during a clinician visit (e.g., yearly checkup), the patient and clinician may determine whether further changes are appropriate. Accordingly, in some examples, IMD 102 may be configured to transition from induction period 406 to maintenance period 410 without patient provided checkpoint (e.g., without checkpoint 408).

Figure 5:
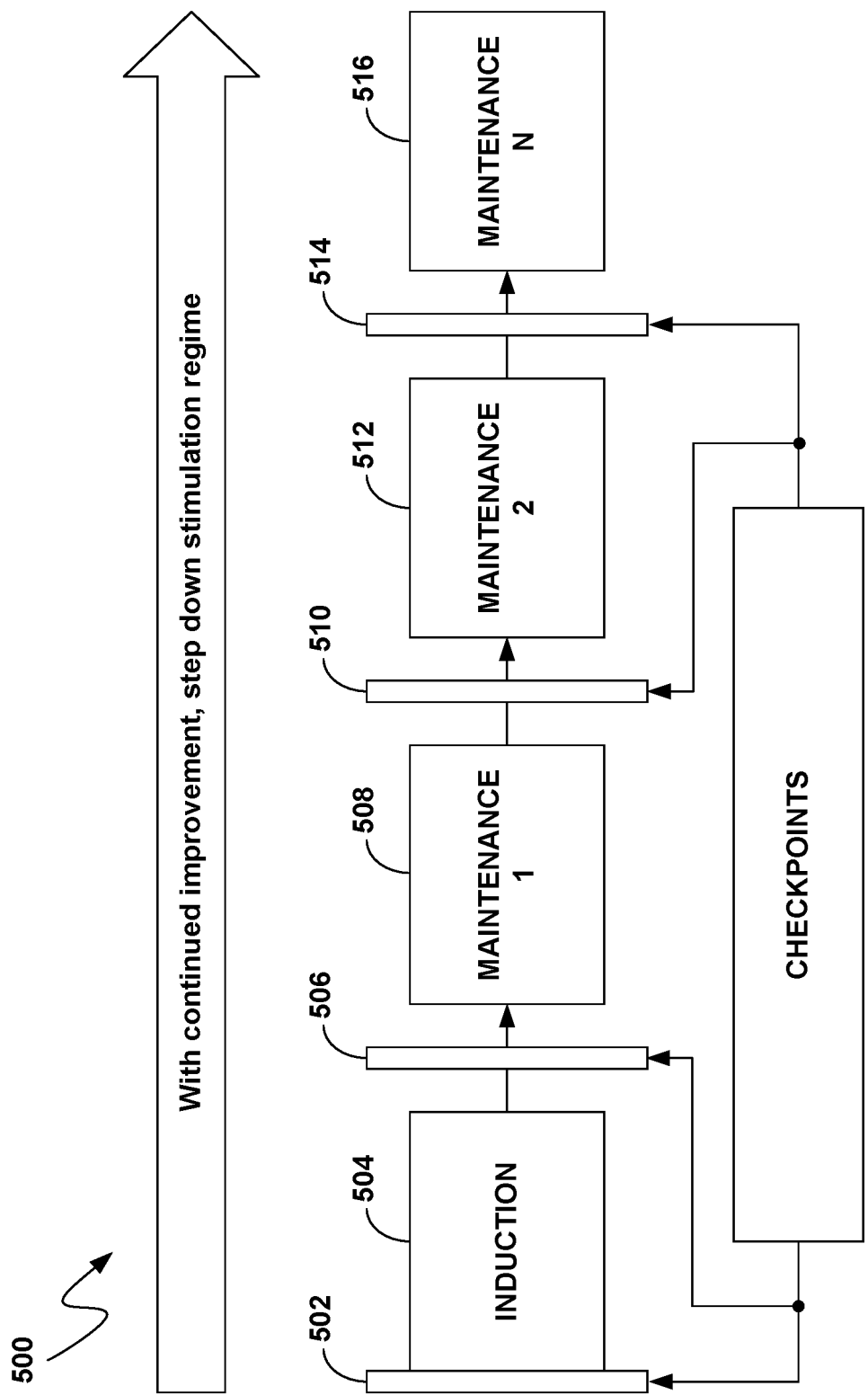
FIG. 5 is another flowchart of a method of optimizing treatment for a medical device, according to one or more examples.

Referring to FIG. 5, a flowchart of a method 500 of optimizing treatment for a medical device is depicted, according to one or more examples. Method 500 generally includes a plurality of checkpoints, such as checkpoint 502, 506, 510, and 514, an induction period 504, and a plurality of maintenance periods, such as first maintenance period 508, second maintenance period 512, and so on to third maintenance period 516 (illustrated as maintenance N to denote the open-ended structure of the maintenance periods).

In one or more examples, as mentioned above and also referring to FIG. 4, first maintenance 508, second maintenance 512, and third maintenance 516 can be included in maintenance period 410 until the end of therapy life. Likewise, checkpoints 502, 506, 510, and 514 can be included in checkpoint 408.

In operation, method 500 operates after implant, beginning at an evaluation at checkpoint 502 to decide whether to proceed to induction period 504. For example, checkpoint 502 can be the initial implant.

In one example, induction period 504 is the highest stimulation regimen and is set for 1× daily. In one example, the amplitude in induction period 504 is the maximum tolerable stimulation (e.g., amplitude, energy, etc.) to the patient. In one example, the amplitude in induction period 504 is at a sensory threshold.

From induction period 504, method 500 proceeds to checkpoint 506. At checkpoint 506, an evaluation is made as to whether method 500 should remain in induction period 504 or move to first maintenance period 508.

In some examples, first maintenance period 508 comprises a relatively less stimulation regimen (e.g., in terms of stimulation session duration or stimulation session occurrence) than induction period 504. For example, the stimulation amplitude can be the same as in induction period 504, but is set to be less often, such as every other day. In some examples, the stimulation amplitude can be relatively less than induction period 504, and/or in combination with a lesser occurrence.

From first maintenance period 508, method 500 proceeds to checkpoint 510. At checkpoint 510, an evaluation is made (e.g., by the patient or clinician) as to whether method 500 should remain in first maintenance period 508 or move to second maintenance period 512.

In some examples, and similar to the contrast between induction period 504 and first maintenance period 508, second maintenance period 512 comprises a relatively lesser stimulation regimen than first maintenance period 508. For example, the regimen at second maintenance period 512 can be at an equal or lower amplitude compared to an amplitude during first maintenance period 508 and a stimulation session occurrence of every third day.

From second maintenance period 512, method 500 proceeds to checkpoint 514. At checkpoint 514, an evaluation is made as to whether method 500 should remain in second maintenance period 512 or move to third maintenance period 516.

In some examples, and similar to the contrast between first maintenance period 508 and second maintenance period 512, third maintenance period 516 comprises a relatively lesser stimulation regimen (e.g., lesser stimulation session duration, stimulation session occurrence, and/or amplitude) than second maintenance period 512. For example, the regimen at third maintenance period 516 can be at an equal or lesser amplitude as second maintenance period 512 and a stimulation occurrence of every week.

While three maintenance periods are illustrated, additional or fewer maintenance periods can be implemented. For example, the number of maintenance periods can be defined to be [1 hour daily→30 minutes daily→30 minutes weekly→30 minutes every other week→30 minutes monthly].

In one or more examples, checkpoints 502, 506, 510, and 514 can include visits from physicians, tele-visits, or algorithm-evoked. Checkpoints 502, 506, 510, and 514 may be determined based on patient-perceived or measured improvement. Checkpoints 502, 506, 510, and 514 may further check or evaluate a sensory threshold to readjust, such as moving to subsensory instead of a fewer number of days.

Further, different types of stimulation corresponding to different period length or timing can be provided at each maintenance period. In some examples, each maintenance period can reflect a changed frequency or amplitude.

For a disease like fecal incontinence, the method duration can be slower than a method duration for urinary incontinence. For example, a fecal incontinence therapy might need longer stimulation for a longer timeframe, thereby requiring a longer induction period (e.g., a longer amount of time before the induction period is complete) and longer maintenance periods (e.g., a longer amount of time before the therapy is reduced in the multiple maintenance periods). A urinary incontinence induction period may be relatively shorter. Likewise, a mixed incontinence, i.e., urinary and fecal incontinence, induction period can be further distinguished in relative length. As described here, the relative period lengths can be further specialized according to particular symptoms or particularities of the disease.

In some examples, criteria to move between maintenance periods can be based on patient input or other patient-specific evaluation. For example, if a patient set a goal of no leaks and the goal is achieved, the stimulation parameters can move to a relatively stepped-down dose maintenance periods (e.g., stepped down in terms of reduced stimulation session duration, stimulation session occurrence, or amplitude). Similarly, if leaks return, then the stimulation parameters can move to a relatively stepped-up maintenance period (e.g., stepped up in terms of increased stimulation session duration, stimulation session occurrence, or amplitude). Other stimulation parameters can likewise be adjusted using any other suitable measure. In some examples, a patient or physician can set a goal (or the system can be pre-populated with such goals) of a reduction in symptoms by a given percentage (e.g. 10%).

The criteria to move between maintenance periods may be a question to the patient rating their perception of their therapy. If the patient indicates therapy is positive, the therapy can be stepped down (e.g., stimulation session duration, stimulation session occurrence, amplitude, etc. may be reduced). If the patient indicates therapy is negative, the therapy can be stepped up (e.g., stimulation session duration, stimulation session occurrence, amplitude, etc. may be increased).

Accordingly, method 500 operates by continually improving patient therapy and stepping down the stimulation regimen. By the maintenance period and check point structure of described in this disclosure, the number of stimulations and/or dosing is reduced. However, as needed, therapy can be stepped back up by returning to a previous (higher stim or dose) maintenance period if no improvement is attained or if improvement is lost.

As described above with respect to FIG. 4, in some examples, checkpoint 408 (FIG. 4) may be skipped. Similarly, in some examples, one or more of checkpoints 502, 506, 510, and 514 may be skipped. For instance, where there are multiple maintenance periods (e.g., maintenance periods 508, 512, and 516), IMD 102 may automatically or through control from the clinician transition through the maintenance periods without requiring checkpoints 506, 510, and 514, respectively. Accordingly, in some examples, IMD 102 may be configured to transition from the first maintenance period 508 to the second maintenance period 512 without patient provided checkpoint (e.g., without checkpoint 506).

Figure 6:
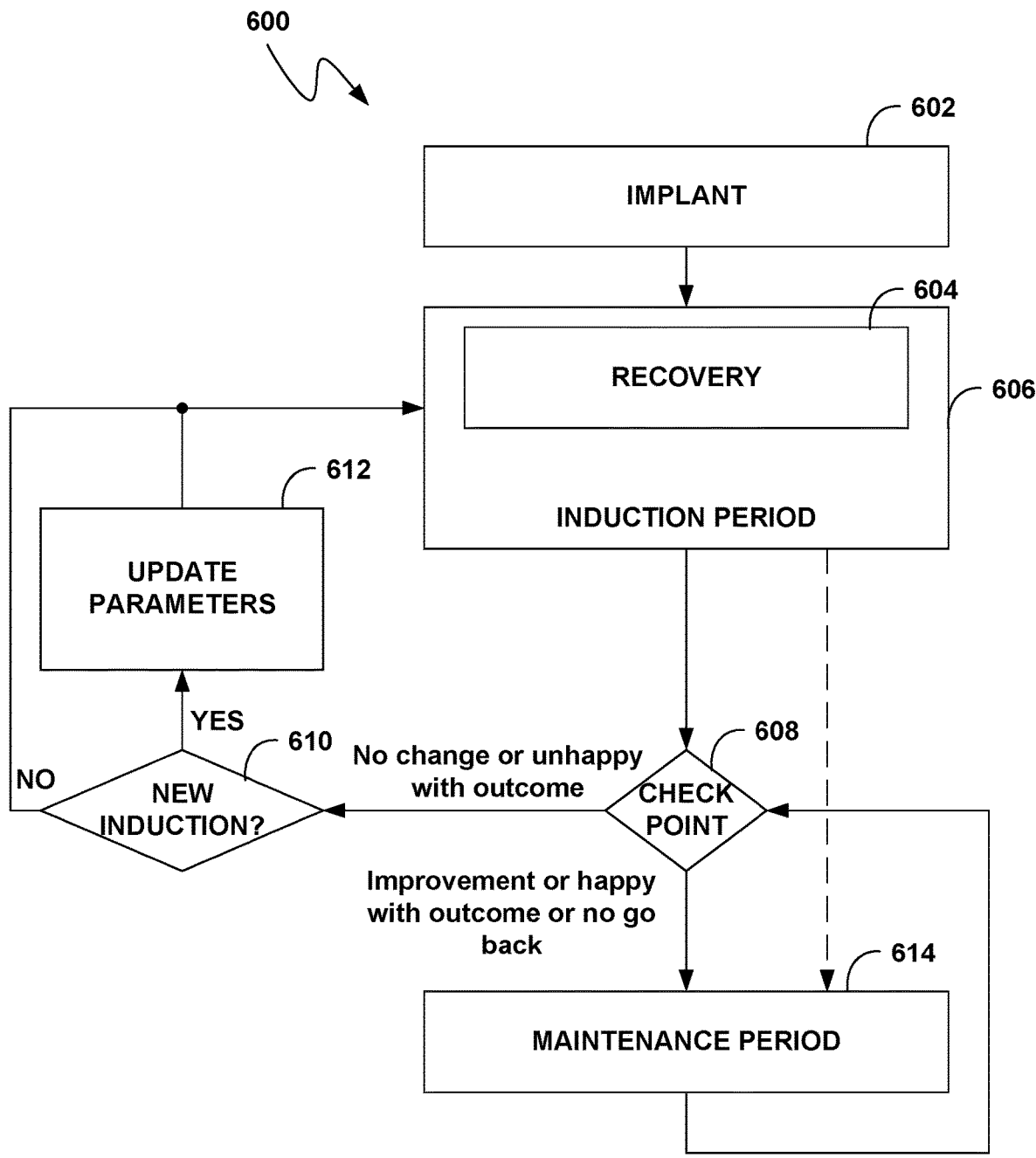
FIG. 6 is another flowchart of a method of optimizing treatment for a medical device, according to one or more examples.

FIG. 6 is another flowchart of a method of optimizing treatment for a medical device, according to one or more examples. In the example of FIG. 6, implant period 602, recovery period 604, induction period 606, checkpoint 608 may be substantially the same as implant period 402, recovery period 404, induction period 406, and checkpoint 408 of FIG. 4. However, in FIG. 6, there may be a plurality of induction periods. Also, maintenance period 614 of FIG. 6 may be substantially the same as maintenance period 410 of FIG. 4.

As illustrated in FIG. 6, at checkpoint 608, for "No change or unhappy with outcome" if there is no or insufficient symptom relief or if it is determined at checkpoint 608 that the patient is unhappy with the outcome of therapy, processing circuitry (e.g., any one or combination of processing circuitry 250 or processing circuitry of programmers 104 or 108) may determine whether new or adjusted induction parameters are appropriate (610). For example, if a threshold amount of time has passed (e.g., more than 3 weeks) and the patient is still indicating that there is no symptom relief or the patient is unhappy with the outcome of therapy, the processing circuitry may determine that update to parameters is appropriate. However, if the threshold amount of time has not passed, then the processing circuitry may determine that update to the parameters is not appropriate.

As another example, if the patient has entered a threshold number of times that there is no symptom relief or that the patient is unhappy with the outcome of therapy (e.g., "No change or unhappy with outcome" as shown in FIG. 6), then the processing circuitry may determine that update to the parameters is appropriate. However, if the threshold number of times has not been reached, then the processing circuitry may determine that update to the parameters is not appropriate.

If the patient experiences improvement or is happy with the outcome, or in some examples, if the patient does not want to return to the induction period, the processing circuitry may enter the maintenance period (614). The processing circuitry may deliver stimulation in accordance with the maintenance period, and periodically check, at checkpoint 608, if any changes to therapy are in order.

If the processing circuitry determines that new induction parameters are desirable (YES of 610), then the processing circuitry may update the parameters (612), and start a new induction period 606 with delivery of therapy in accordance with the updated parameters. For the maintenance period 614 (or the plurality of maintenance periods such as those of FIG. 5), the processing circuitry may determine stimulation parameters based on the updated stimulation parameters determined as part of step 612. However, if the processing circuitry determines that new induction parameters are not desirable (NO of 610), then the processing circuitry may start a new induction period 606 with no change in stimulation parameters.

Accordingly, after the first induction period and prior to the first maintenance period, the processing circuitry may determine to update the set of stimulation parameters (YES of 610), and based on the determination to update the set of stimulation parameters, the processing circuitry may determine an updated set of stimulation parameters (612). During a second induction period, the processing circuitry may initiate electrical stimulation therapy according to the updated set of stimulation parameters. In such examples, during the first maintenance period, to determine the adjustment to the set of stimulation parameters as the first maintenance period stimulation parameters to reduce the electrical stimulation therapy from the induction period, the processing circuitry may be configured to, during the first maintenance period, determine an adjustment to the updated set of stimulation parameters as the first maintenance period stimulation parameters to reduce the electrical stimulation therapy from the second induction period.

However, in some examples, after the induction period and prior to the first maintenance period, the processing circuitry may determine not to update the set of stimulation parameters (NO of 610). In such examples, based on the determination not to update the set of stimulation parameters, the processing circuitry may maintain the electrical stimulation therapy parameters from the induction period (e.g., return back to induction period 606 without changes to the stimulation parameters).

Similar to FIG. 4, FIG. 6 includes a dashed line from induction period 606 to maintenance period 614 to indicate that in some examples checkpoint 608 may be skipped. For example, the clinician may program IMD 102 to automatically transition from induction period 606 to maintenance period 610 after a certain amount of time or after a certain number of times that the patient failed to respond during checkpoint 608. There may be various ways in which the clinician may determine how long to wait or how many failed checkpoint instances there are before automatically transitioning IMD 102 from the induction period to the maintenance period, such as those described above with respect to FIG. 4.

In some examples, rather than automatically transitioning from induction period 606 to maintenance period 610, the patient may request the clinician to transition from induction period 606 to maintenance period 610. In some examples, the clinician may remotely control IMD 102 to transition from induction period 606 to maintenance period 610. In some examples, the clinician may transition IMD 102 from induction period 606 to maintenance period 410 during a clinician visit. As illustrated, after maintenance period 610, there is another checkpoint 608. In examples where checkpoint 608 is skipped, during a clinician visit (e.g., yearly checkup), the patient and clinician may determine whether further changes are appropriate. Accordingly, in some examples, IMD 102 may be configured to transition from induction period 606 to maintenance period 610 without patient provided checkpoint (e.g., without checkpoint 608).

Figure 7:
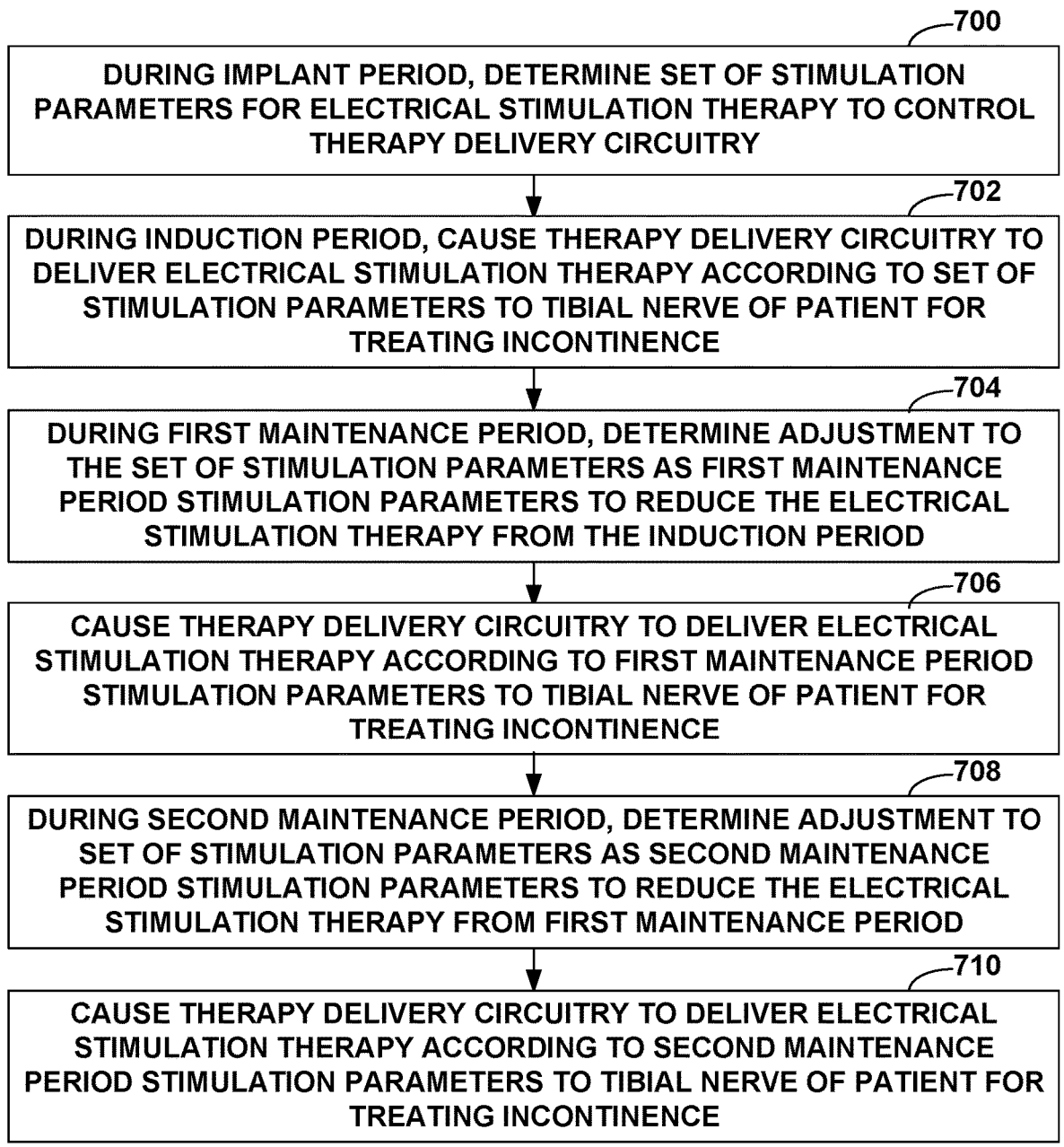
FIG. 7 is a flowchart illustrating an example method of treating incontinence.

FIG. 7 is a flowchart illustrating an example method of treating incontinence. The example of FIG. 7 is described with respect to processing circuitry. Examples of the processing circuitry include one or any combination of processing circuitry 250 or processing circuitry of programmers 104 or 108, or possibly other processing circuitry such as processing circuitry in the network or cloud.

During an implant period, the processing circuitry may be configured to determine a set of stimulation parameters for electrical stimulation therapy to control therapy delivery circuitry 254 (e.g., according to a sensory or motor threshold) (700). For example, during implant or during the clinic visit where IMD 152 is implanted, the HCP may use programmer 104 or 108 with a baseline amplitude, pulse width, and frequency, and increase one or more of the amplitude, pulse width, and frequency until the patient indicates that the patient is feeling the therapy (e.g., sensory threshold) or there is visible muscle movement or there is an electromyography (EMG) signal (e.g., motor threshold). During an induction period, the processing circuitry may cause therapy delivery circuitry 254 to deliver electrical stimulation therapy according to the set of stimulation parameters to a tibial nerve of a patient for treating the incontinence (702).

Delivery circuitry 254 delivering electrical stimulation therapy to a tibial nerve includes examples where delivery circuitry 254 delivers electrical stimulation therapy to one tibial nerve or both tibial nerves, or bilateral stimulation. For instance, delivery circuitry 254 may alternate delivery of stimulation to the tibial nerves.

During a first maintenance period, the processing circuitry may determine an adjustment to the one or more of the set of stimulation parameters as first maintenance period stimulation parameters (e.g., adjust one or more amplitude, stimulation session occurrence, stimulation session duration, etc.) to reduce the electrical stimulation therapy from the induction period (704). In some examples, during the induction period and prior to the first maintenance period, the processing circuitry may receive an indication that the patient is experiencing improvement in outcome of therapy. In such examples, the processing circuitry may determine the adjustment to the set of stimulation parameters as the first maintenance period stimulation parameters in response to the patient indicating experiencing improvement in outcome of therapy.

In one or more examples, to determine the adjustment to the set of stimulation parameters as first maintenance period stimulation parameters to reduce the electrical stimulation therapy from the induction period, the processing circuitry may access memory that stores information for different sets of stimulation parameters associated with different periods, and the processing circuitry may determine the adjustment to the set of stimulation parameters based on the parameters associated with the first maintenance period. As another example, to determine the adjustment to the set of stimulation parameters as first maintenance period stimulation parameters to reduce the electrical stimulation therapy from the induction period, the processing circuitry may receive information indicative of the adjustment to the set of stimulation parameters as first maintenance period stimulation parameters.

The processing circuitry may cause therapy stimulation circuitry 254 to deliver the electrical stimulation therapy according to the first maintenance period stimulation parameters to the tibial nerve of the patient for treating the incontinence (706). In this way, there can be a reduction in amount of stimulation that is delivered to the patient without impact on therapy efficacy, which in turn can increase operational life of IMD 152. Similar to above for the induction period, during the first maintenance period, delivery circuitry 254 delivering electrical stimulation therapy to a tibial nerve includes examples where delivery circuitry 254 delivers electrical stimulation therapy to one tibial nerve or both tibial nerves, or bilateral stimulation. For instance, delivery circuitry 254 may alternate delivery of stimulation to the tibial nerves.

During a second maintenance period, the processing circuitry may determine an adjustment to the set of stimulation parameters as second maintenance period stimulation parameters to reduce the electrical stimulation therapy from the first maintenance period (708). In some examples, prior to the second maintenance period, the processing circuitry may receive indication that the patient is happy with therapy outcome. In such examples, determining the adjustment to the set of stimulation parameters as the second maintenance period stimulation parameters to reduce the electrical stimulation therapy (e.g., reduce amplitude, stimulation session occurrence, stimulation session duration, etc.) from the first maintenance period may include determining the adjustment to the set of stimulation parameters as the second maintenance period stimulation parameters to reduce the electrical stimulation therapy from the first maintenance period in response to receiving the indication that the patient is happy with the therapy outcome.

The processing circuitry may cause therapy delivery circuitry 254 to deliver the electrical stimulation therapy according to the second maintenance period stimulation parameters to the tibial nerve of the patient for treating the incontinence (710). In this way, there can be a further reduction in an amount of stimulation that is delivered to the patient without impact on therapy efficacy, which in turn can further increase operational life of IMD 152. Similar to above for the induction period and the first maintenance period, during the second maintenance period, delivery circuitry 254 delivering electrical stimulation therapy to a tibial nerve includes examples where delivery circuitry 254 delivers electrical stimulation therapy to one tibial nerve or both tibial nerves, or bilateral stimulation. For instance, delivery circuitry 254 may alternate delivery of stimulation to the tibial nerves.

In some examples, there may be one induction period, but the techniques are not so limited. For example, after a first induction period and prior to the first maintenance period, the processing circuitry may determine to update one or more parameters of the set of stimulation parameters, based on the determination to update the set of stimulation parameters, the processing circuitry may determine an updated set of stimulation parameters, and during a second induction period, the processing circuitry may initiate electrical stimulation therapy according to the updated set of stimulation parameters. In such examples, during the first maintenance period, the processing circuitry may determine an adjustment to the updated set of stimulation parameters as the first maintenance period stimulation parameters to reduce the electrical stimulation therapy from the second induction period. In some examples, the processing circuitry may determine to update the set of stimulation parameters in response the patient indicating that there is no change or that the patient is unhappy with outcome of therapy.

However, in some cases, after the induction period and prior to the first maintenance period, the processing circuitry may determine not to update the set of stimulation parameters, and based on the determination not to update the set of stimulation parameters, the processing circuitry may maintain the electrical stimulation therapy from the induction period.

In some examples, the example methods of FIGS. 4-7 can begin as a user-interactive or manual process, and become automated as defined by the physician boundaries (e.g., boundaries of stimulation parameters that the physician defined so that parameters cannot exceed boundaries) and as accepted by the patient. Physician boundaries may be based on symptom measures; e.g. number of leaks, frequency, urgency events, etc. Other criteria such as number of catheterizations, pain score, etc. can likewise be utilized. For example, a physician can define certain symptom measures and certain changes to the workflow or the various periods based on those measures. The example systems and methods can operate up to those boundaries.

Accordingly, in one or more examples described in this disclosure, patients are able to receive therapy in only one in office visit (for the implant), which may result in the time to when the patient experiences symptom relief being reduced and accelerated. Moreover, IMDs, like IMD 102, may be configured according to a flexible therapy regimen based on the particular disease burden of the patient. Also, recording and analyzing programming and patient diaries can provide more effective programming to future patients, such as for setting the initial parameters or parameters during the induction period. In some examples, workflows supported by IMD 102 can be adjusted per indication and/or symptom.

As described above, in some examples, but not necessarily all, patients may receive therapy much faster than some other techniques. For example, traditional therapies can include a lengthy induction period in which at least one additional clinic visit is required to test the initial stimulation parameters and/or turn the device on.

In one or more examples described in this disclosure, initial stimulation parameters can be defined without a follow-up visit, and the device can be turned on at the time of the patient or physician's choosing. More particularly, by one or more checkpoints after induction, which is automated according to physician-defined or pre-defined parameters and includes perceived or measured user input, therapy can be initiated quickly and safely. For instance, in some techniques, any change in therapy or reconfiguration of IMD 102 for an advanced therapy may require a follow-up visit to the HCP. With the example techniques, changes to the therapy can be performed safely and quickly, without the patient necessarily following up with the HCP.

Further, the periodic checkpoints and plurality of maintenance periods described herein help transition patients to more suitable therapies much faster than other techniques. In some cases, some traditional therapies include providing a continuous stimulation, which impacts the life of IMD 102 or its available power, as well as the effectiveness of therapy, as the patient bodies can adapt to continuous stimulation. By having periodic checkpoints and plurality of maintenance periods where therapy may be adjusted, the chances of adaptation (also called accommodation) may be reduced.

For example, traditional therapies typically include recursive training and then maintenance periods. If therapy is not working at a given maintenance period, the patient may have needed to go back to a (sometimes lengthy) training period, often in which the patient is not being provided therapy. Moreover, the maintenance period in existing techniques is typically a take-it-or-leave-it single period. In one or more examples described herein, by utilizing the plurality of checkpoints according to physician-defined or pre-defined parameters and which include perceived or measured user input, the patient can be quickly and safely stepped between therapies based on the patient's disease burden according to the plurality of maintenance periods. Patient therapy can accordingly be favorably stepped down faster than existing techniques. Patient therapy can also be efficiently stepped up according to the plurality of maintenance periods, should the disease burden require, faster than existing techniques. The example techniques therefore offer more fine-tuned treatment than existing therapies.

Some existing techniques provide, for example, therapies that operate according to a single pre-defined path of maintenance protocols, such as continuous stimulation, no stimulation, continuous stimulation, then intermittent stimulation. Still other existing techniques provide, for example, therapies that operate by providing stimulation that cycles delivery at a subsensory threshold, allowing the patient to "revert" back to the sensory threshold, thereby drastically increasing stimulation. In one or more examples described herein, including a plurality of maintenance periods and integrated checkpoints can step up and/or step down therapy, instead of drastically increasing stimulation, between the plurality of maintenance periods, thereby providing a more flexible, responsive, and fine-tuned therapy for the patient.

The following table shows examples of traditional therapies with respect to the number of visits and weeks before therapy can start. With the example techniques described in this disclosure, the number of visits may be reduced and the time before therapy can start can be reduced.

TABLE 1

| Therapy | Visits in year 1 | Weeks to Therapy | Visits in 3 years |
| --- | --- | --- | --- |
| SNM | 4 | 1 week | 7 |
| Botox | 2 | 0 weeks | 6 |
| PTNM (Percutaneous Tibial Neuromodulation) | 21 | 4-8 weeks | 45 |

The example techniques described in this disclosure may provide one or more advantages. The following describes some example advantages. The example techniques described in this disclosure should not be considered limited to providing the following advantages, or be considered as requiring that the following advantages be present. The following advantages are provided merely as examples.

In one or more examples, because of how a tibial IMD (e.g., IMD 152) is implanted and the nerve at issue, the tibial IMD can be turned on immediately. Accordingly, symptom relief can be implemented immediately after implant. However, it may be possible that when implanted, an HCP can configure the IMD to start in a certain number of days and/or time from implant, or the HCP can also configure the IMD to turn on at a specific day and time of the patient or HCP's choosing.

In some devices, which can be voltage-controlled, there is a risk that electrode encapsulation changes with that stimulation. In some examples, the tibial IMD (e.g., IMD 152) may be implemented as constant current, thereby alleviating any impedance concerns. However, voltage-controlled examples of IMD 152 are possible.

As described above, the workflows described herein can reduce patient-HCP visit burden. The IMD 152 may be outcome-oriented such that the IMD 152 is programmed towards patient goals to improve efficacy of treatment.

In some examples, a high stimulation regimen for an induction period 406 can potentially increase the speed by which patients see meaningful symptom relief. Also, patient-specific titration of therapy is implemented in an induction period 406 and maintenance period 410, including the plurality of maintenance periods 504, 508, 512, and 516.

In some examples, previous data and population statistics can be interrogated to propose more efficient therapy regimens for future patients (e.g., for induction period 406 or as initial parameters after implant). Previous data and population statistics may also be utilized to determine when checkpoints should be given. For instance, previous data and population statistics may be utilized to determine when checkpoint 408, checkpoints 506, 510, and 514, and checkpoint 608 are evaluated. In some examples, patients can be weaned off of continuous therapy, which can not only increase the longevity of the IMD (e.g., how long the IMD can operate before replacement or how long the IMD can operate before recharging), but also avoids over-stimulating nerves for therapy, as some patients may lose therapy efficacy over time due to over-stimulation of nerves (e.g., due to accommodation).

The following describes example techniques that may be performed separately or together in any combination.

Clause 1. A medical system for treating incontinence comprising: an implantable medical device (IMD) implantable proximate to a tibial nerve of a patient, the IMD comprising therapy delivery circuitry configured to provide electrical stimulation therapy proximate the tibial nerve of the patient for treating incontinence; and processing circuitry configured to: during an implant period, determine a set of stimulation parameters to control the therapy delivery circuitry, during an induction period after the implant period, initiate electrical stimulation therapy according to the set of stimulation parameters, during a first maintenance period, determine an adjustment to the set of stimulation parameters as first maintenance period stimulation parameters to reduce the electrical stimulation therapy from the induction period, wherein the therapy delivery circuitry provides the electrical stimulation therapy according to the first maintenance period stimulation parameters, and during a second maintenance period, determine an adjustment to the set of stimulation parameters as second maintenance period stimulation parameters to reduce the electrical stimulation therapy from the first maintenance period, wherein the therapy delivery circuitry provides the electrical stimulation therapy according to the second maintenance period stimulation parameters.

Clause 2. The medical system of clause 1, further comprising a programmer, wherein the programmer is configured to: during the induction period and prior to the first maintenance period, receive an indication that the patient is experiencing improvement in outcome of therapy, wherein the processing circuitry is configured to determine the adjustment to the set of stimulation parameters as the first maintenance period stimulation parameters in response to the patient indicating experiencing improvement in outcome of therapy.

Clause 3. The medical system of any of clauses 1 and 2, wherein the induction period comprises a first induction period, and wherein the processing circuitry is configured to: after the first induction period and prior to the first maintenance period, determine to update the set of stimulation parameters; based on the determination to update the set of stimulation parameters, determine an updated set of stimulation parameters; and during a second induction period, initiate electrical stimulation therapy according to the updated set of stimulation parameters, wherein, during the first maintenance period, to determine the adjustment to the set of stimulation parameters as the first maintenance period stimulation parameters to reduce the electrical stimulation therapy from the induction period, the processing circuitry is configured to, during the first maintenance period, determine an adjustment to the updated set of stimulation parameters as the first maintenance period stimulation parameters to reduce the electrical stimulation therapy from the second induction period.

Clause 4. The medical system of clause 3, wherein to determine to update the set of stimulation parameters, the processing circuitry is configured to determine to update the set of stimulation parameters in response to the patient indicating that there is no change.

Clause 5. The medical system of any of clauses 1-4, wherein the processing circuitry is configured to: after the induction period and prior to the first maintenance period, determine not to update the set of stimulation parameters; and based on the determination not to update the set of stimulation parameters, maintain the electrical stimulation therapy from the induction period.

Clause 6. The medical system of any of clauses 1-5, wherein the processing circuitry is further configured to: during a recovery period, receive an adjustment to the set of stimulation parameters to increase the electrical stimulation therapy based on patient adaptations with the IMD.

Clause 7. The medical system of clause 6, wherein the recovery period overlaps with the induction period.

Clause 8. The medical system of any of clauses 1-7, wherein the processing circuitry is further configured to: receive a command to return to the first maintenance period from the second maintenance period.

Clause 9. The medical system of any of clauses 1-8, wherein the processing circuitry is further configured to: during a third maintenance period, determine an adjustment to the set of stimulation parameters as third maintenance period stimulation parameters to reduce the electrical stimulation therapy from the second maintenance period.

Clause 10. The medical system of any of clauses 1-9, wherein the first maintenance period stimulation parameters include one or both of: a stimulation session duration less than a stimulation session duration of the induction period stimulation parameters, or a stimulation session occurrence less often than a stimulation session occurrence of the induction period stimulation parameters.

Clause 11. The medical system of any of clauses 1-10, wherein the second maintenance period stimulation parameters include one or both of: a stimulation session duration less than a stimulation session duration of the first maintenance period stimulation parameters, or a stimulation session occurrence less often than a stimulation session occurrence of the first maintenance period stimulation parameters.

Clause 12. The medical system of any of clause 1-11, wherein the electrical stimulation therapy is configured to treat fecal incontinence and urinary incontinence, wherein a stimulation session duration in the set of stimulation parameters to treat fecal incontinence is longer than a stimulation session duration in the set of stimulation parameters to treat urinary incontinence such that the electrical stimulation therapy is provided during a filling phase when the bowel is full.

Clause 13. The medical system of any of clauses 1-11, wherein the electrical stimulation therapy configured to treat fecal incontinence and urinary incontinence, wherein a stimulation session occurrence in the set of stimulation parameters to treat fecal incontinence is more often than a stimulation session occurrence in the set of stimulation parameters to treat urinary incontinence such that the electrical stimulation therapy is provided during a filling phase when the bowel is full.

Clause 14. The medical system of any of clauses 1-13, wherein the processing circuitry is configured to: prior to the second maintenance period, receive indication that the patient is satisfied with therapy outcome, wherein to determine the adjustment to the set of stimulation parameters as the second maintenance period stimulation parameters to reduce the electrical stimulation therapy from the first maintenance period, the processing circuitry is configured to determine the adjustment to the set of stimulation parameters as the second maintenance period stimulation parameters to reduce the electrical stimulation therapy from the first maintenance period in response to receiving the indication that the patient is satisfied with the therapy outcome.

Clause 15. The medical system of any of clauses 1-14, wherein one of: the IMD includes the processing circuitry; a programmer of the medical system includes the processing circuitry; or a combination of the IMD and the programmer includes the processing circuitry.

Clause 16. A method for treating incontinence, the method comprising: during an implant period, determining, with processing circuitry, a set of stimulation parameters for electrical stimulation therapy to control a therapy delivery circuitry; during an induction period after the implant period, causing, with the processing circuitry, the therapy delivery circuitry to deliver electrical stimulation therapy according to the set of stimulation parameters to a tibial nerve of a patient for treating the incontinence; during a first maintenance period, determining, with the processing circuitry, an adjustment to the set of stimulation parameters as first maintenance period stimulation parameters to reduce the electrical stimulation therapy from the induction period; causing, with the processing circuitry, the therapy delivery circuitry to deliver the electrical stimulation therapy according to the first maintenance period stimulation parameters to the tibial nerve of the patient for treating the incontinence; during a second maintenance period, determining, with the processing circuitry, an adjustment to the set of stimulation parameters as second maintenance period stimulation parameters to reduce the electrical stimulation therapy from the first maintenance period; and causing, with the processing circuitry, the therapy delivery circuitry to deliver the electrical stimulation therapy according to the second maintenance period stimulation parameters to the tibial nerve of the patient for treating the incontinence.

Clause 17. The method of clause 16, further comprising: during the induction period and prior to the first maintenance period, receiving an indication that the patient is experiencing improvement in outcome of therapy, determining the adjustment to the set of stimulation parameters as the first maintenance period stimulation parameters comprises determining the adjustment to the set of stimulation parameters as the first maintenance period stimulation parameters in response to the patient indicating experiencing improvement in outcome of therapy.

Clause 18. The method of any of clauses 16 and 17, wherein the induction period comprises a first induction period, the method further comprising: after the first induction period and prior to the first maintenance period, determining to update the set of stimulation parameters; based on the determination to update the set of stimulation parameters, determining an updated set of stimulation parameters; and during a second induction period, initiating electrical stimulation therapy according to the updated set of stimulation parameters, wherein, during the first maintenance period, determining the adjustment to the set of stimulation parameters as the first maintenance period stimulation parameters to reduce the electrical stimulation therapy from the induction period comprises, during the first maintenance period, determining an adjustment to the updated set of stimulation parameters as the first maintenance period stimulation parameters to reduce the electrical stimulation therapy from the second induction period.

Clause 19. The method of clause 18, wherein determining to update the set of stimulation parameters comprises determining to update the set of stimulation parameters in response to the patient indicating that there is no change.

Clause 20. The method of any of clauses 16-19, further comprising: after the induction period and prior to the first maintenance period, determining not to update the set of stimulation parameters; and based on the determination not to update the set of stimulation parameters, maintaining the electrical stimulation therapy from the induction period.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A medical system for treating incontinence comprising:
an implantable medical device (IMD) implantable proximate to a tibial nerve of a patient, the IMD comprising therapy delivery circuitry configured to provide electrical stimulation therapy proximate the tibial nerve of the patient for treating incontinence; and
processing circuitry configured to:
during an implant period, determine a set of stimulation parameters to control the therapy delivery circuitry,
during an induction period after the implant period, initiate electrical stimulation therapy according to the set of stimulation parameters,
during a first maintenance period, determine an adjustment to the set of stimulation parameters as first maintenance period stimulation parameters to reduce the electrical stimulation therapy from the induction period, wherein the therapy delivery circuitry provides the electrical stimulation therapy according to the first maintenance period stimulation parameters, and
during a second maintenance period, determine an adjustment to the set of stimulation parameters as second maintenance period stimulation parameters to reduce the electrical stimulation therapy from the first maintenance period, wherein the therapy delivery circuitry provides the electrical stimulation therapy according to the second maintenance period stimulation parameters.

2. The medical system of claim 1, further comprising a programmer, wherein the programmer is configured to:
during the induction period and prior to the first maintenance period, receive an indication that the patient is experiencing improvement in outcome of therapy,
wherein the processing circuitry is configured to determine the adjustment to the set of stimulation parameters as the first maintenance period stimulation parameters in response to the patient indicating experiencing improvement in outcome of therapy.

3. The medical system of claim 1, wherein the induction period comprises a first induction period, and wherein the processing circuitry is configured to:
- after the first induction period and prior to the first maintenance period, determine to update the set of stimulation parameters;
- based on the determination to update the set of stimulation parameters, determine an updated set of stimulation parameters; and
- during a second induction period, initiate electrical stimulation therapy according to the updated set of stimulation parameters,
- wherein, during the first maintenance period, to determine the adjustment to the set of stimulation parameters as the first maintenance period stimulation parameters to reduce the electrical stimulation therapy from the induction period, the processing circuitry is configured to, during the first maintenance period, determine an adjustment to the updated set of stimulation parameters as the first maintenance period stimulation parameters to reduce the electrical stimulation therapy from the second induction period.

4. The medical system of claim 3, wherein to determine to update the set of stimulation parameters, the processing circuitry is configured to determine to update the set of stimulation parameters in response to the patient indicating that there is no change.

5. The medical system of claim 1, wherein the processing circuitry is configured to:
- after the induction period and prior to the first maintenance period, determine not to update the set of stimulation parameters; and
- based on the determination not to update the set of stimulation parameters, maintain the electrical stimulation therapy from the induction period.

6. The medical system of claim 1, wherein the processing circuitry is further configured to:
- during a recovery period, receive an adjustment to the set of stimulation parameters to increase the electrical stimulation therapy based on patient adaptations with the IMD.

7. The medical system of claim 6, wherein the recovery period overlaps with the induction period.

8. The medical system of claim 1, wherein the processing circuitry is further configured to:
- receive a command to return to the first maintenance period from the second maintenance period.

9. The medical system of claim 1, wherein the processing circuitry is further configured to:
- during a third maintenance period, determine an adjustment to the set of stimulation parameters as third maintenance period stimulation parameters to reduce the electrical stimulation therapy from the second maintenance period.

10. The medical system of claim 1, wherein the first maintenance period stimulation parameters include one or both of:
- a stimulation session duration less than a stimulation session duration of induction period stimulation parameters, or
- a stimulation session occurrence less often than a stimulation session occurrence of the induction period stimulation parameters.

11. The medical system of claim 1, wherein the second maintenance period stimulation parameters include one or both of:
- a stimulation session duration less than a stimulation session duration of the first maintenance period stimulation parameters, or
- a stimulation session occurrence less often than a stimulation session occurrence of the first maintenance period stimulation parameters.

12. The medical system of claim 1, wherein the electrical stimulation therapy is configured to treat fecal incontinence and urinary incontinence, wherein a stimulation session duration in the set of stimulation parameters to treat fecal incontinence is longer than a stimulation session duration in the set of stimulation parameters to treat urinary incontinence such that the electrical stimulation therapy is provided during a filling phase when a bowel is full.

13. The medical system of claim 1, wherein the electrical stimulation therapy configured to treat fecal incontinence and urinary incontinence, wherein a stimulation session occurrence in the set of stimulation parameters to treat fecal incontinence is more often than a stimulation session occurrence in the set of stimulation parameters to treat urinary incontinence such that the electrical stimulation therapy is provided during a filling phase when a bowel is full.

14. The medical system of claim 1, wherein the processing circuitry is configured to:
- prior to the second maintenance period, receive indication that the patient is satisfied with therapy outcome,
- wherein to determine the adjustment to the set of stimulation parameters as the second maintenance period stimulation parameters to reduce the electrical stimulation therapy from the first maintenance period, the processing circuitry is configured to determine the adjustment to the set of stimulation parameters as the second maintenance period stimulation parameters to reduce the electrical stimulation therapy from the first maintenance period in response to receiving the indication that the patient is satisfied with the therapy outcome.

15. The medical system of claim 1, wherein the processing circuitry is configured to, at least one of, transition from the induction period to the first maintenance period without patient provided checkpoint, or transition from the first maintenance period to the second maintenance period without patient provided checkpoint.

16. The medical system of claim 1, wherein one of:
the IMD includes the processing circuitry;
a programmer of the medical system includes the processing circuitry; or
a combination of the IMD and the programmer includes the processing circuitry.

17. A method for treating incontinence, the method comprising:
- during an implant period, determining, with processing circuitry, a set of stimulation parameters for electrical stimulation therapy to control a therapy delivery circuitry;
- during an induction period after the implant period, causing, with the processing circuitry, the therapy delivery circuitry to deliver electrical stimulation therapy according to the set of stimulation parameters to a tibial nerve of a patient for treating the incontinence;
- during a first maintenance period, determining, with the processing circuitry, an adjustment to the set of stimulation parameters as first maintenance period stimulation parameters to reduce the electrical stimulation therapy from the induction period;

causing, with the processing circuitry, the therapy delivery circuitry to deliver the electrical stimulation therapy according to the first maintenance period stimulation parameters to the tibial nerve of the patient for treating the incontinence;

during a second maintenance period, determining, with the processing circuitry, an adjustment to the set of stimulation parameters as second maintenance period stimulation parameters to reduce the electrical stimulation therapy from the first maintenance period; and causing, with the processing circuitry, the therapy delivery circuitry to deliver the electrical stimulation therapy according to the second maintenance period stimulation parameters to the tibial nerve of the patient for treating the incontinence.

18. The method of claim 17, further comprising:
during the induction period and prior to the first maintenance period, receiving an indication that the patient is experiencing improvement in outcome of therapy,
determining the adjustment to the set of stimulation parameters as the first maintenance period stimulation parameters comprises determining the adjustment to the set of stimulation parameters as the first maintenance period stimulation parameters in response to the patient indicating experiencing improvement in outcome of therapy.

19. The method of claim 17, wherein the induction period comprises a first induction period, the method further comprising:
after the first induction period and prior to the first maintenance period, determining to update the set of stimulation parameters;
based on the determination to update the set of stimulation parameters, determining an updated set of stimulation parameters; and
during a second induction period, initiating electrical stimulation therapy according to the updated set of stimulation parameters,
wherein, during the first maintenance period, determining the adjustment to the set of stimulation parameters as the first maintenance period stimulation parameters to reduce the electrical stimulation therapy from the induction period comprises, during the first maintenance period, determining an adjustment to the updated set of stimulation parameters as the first maintenance period stimulation parameters to reduce the electrical stimulation therapy from the second induction period.

20. The method of claim 17, further comprising:
after the induction period and prior to the first maintenance period, determining not to update the set of stimulation parameters; and
based on the determination not to update the set of stimulation parameters, maintaining the electrical stimulation therapy from the induction period.

* * * * *